United States Patent
Chan et al.

(10) Patent No.: US 12,310,828 B1
(45) Date of Patent: May 27, 2025

(54) REUSABLE INCONTINENCE UNDERWEAR WITH FECES SENSING

(71) Applicants: Thomas C. Chan, Palo Alto, CA (US); Chi Chen Hsien, Sacramento, CA (US)

(72) Inventors: Thomas C. Chan, Palo Alto, CA (US); Chi Chen Hsien, Sacramento, CA (US)

( * ) Notice: Subject to any disclaimer, the term of this patent is extended or adjusted under 35 U.S.C. 154(b) by 0 days.

(21) Appl. No.: 18/902,769

(22) Filed: Sep. 30, 2024

Related U.S. Application Data

(63) Continuation-in-part of application No. 18/521,183, filed on Nov. 28, 2023, now Pat. No. 12,102,554.

(51) Int. Cl.
*A61F 13/495* (2006.01)
*A61F 13/49* (2006.01)
*A61F 13/84* (2006.01)

(52) U.S. Cl.
CPC ...... *A61F 13/49003* (2013.01); *A61F 13/495* (2013.01); *A61F 13/84* (2013.01)

(58) Field of Classification Search
CPC .. A61F 13/495; A61F 2013/4951–4958; A61F 13/49003; A61F 13/84
See application file for complete search history.

(56) References Cited

U.S. PATENT DOCUMENTS

| | | | |
|---|---|---|---|
| 2013/0165898 A1* | 6/2013 | Rhodes | A61F 13/5644 604/386 |
| 2014/0200538 A1* | 7/2014 | Euliano | A61F 13/42 604/361 |

FOREIGN PATENT DOCUMENTS

WO  WO-2017209346 A1 * 12/2017

* cited by examiner

*Primary Examiner* — Susan S Su
(74) *Attorney, Agent, or Firm* — Silicon Valley Patent Group LLP

(57) ABSTRACT

Apparatuses of reusable incontinence underwear with feces sensing and methods for manufacturing the same are provided. An incontinence underwear includes an interior layer includes an excretion area, where the excretion area includes one or more openings configured to drain excretions of a user away from the interior layer; a middle layer configured to house an excretion collection unit, configured to store the excretions from the interior layer, and the middle layer further includes a feces sensing unit configured to detect feces discharged from the user; a feces monitoring module electrically coupled to the feces sensing unit, configured to monitor the feces sensing unit and communicate status of the feces sensing unit to one or more caregivers; an exterior layer configured to conceal and prevent leakage from the middle layer of the incontinence underwear; and a support frame configured to hold the interior layer, the middle layer and the exterior layer of the incontinence underwear together.

20 Claims, 20 Drawing Sheets

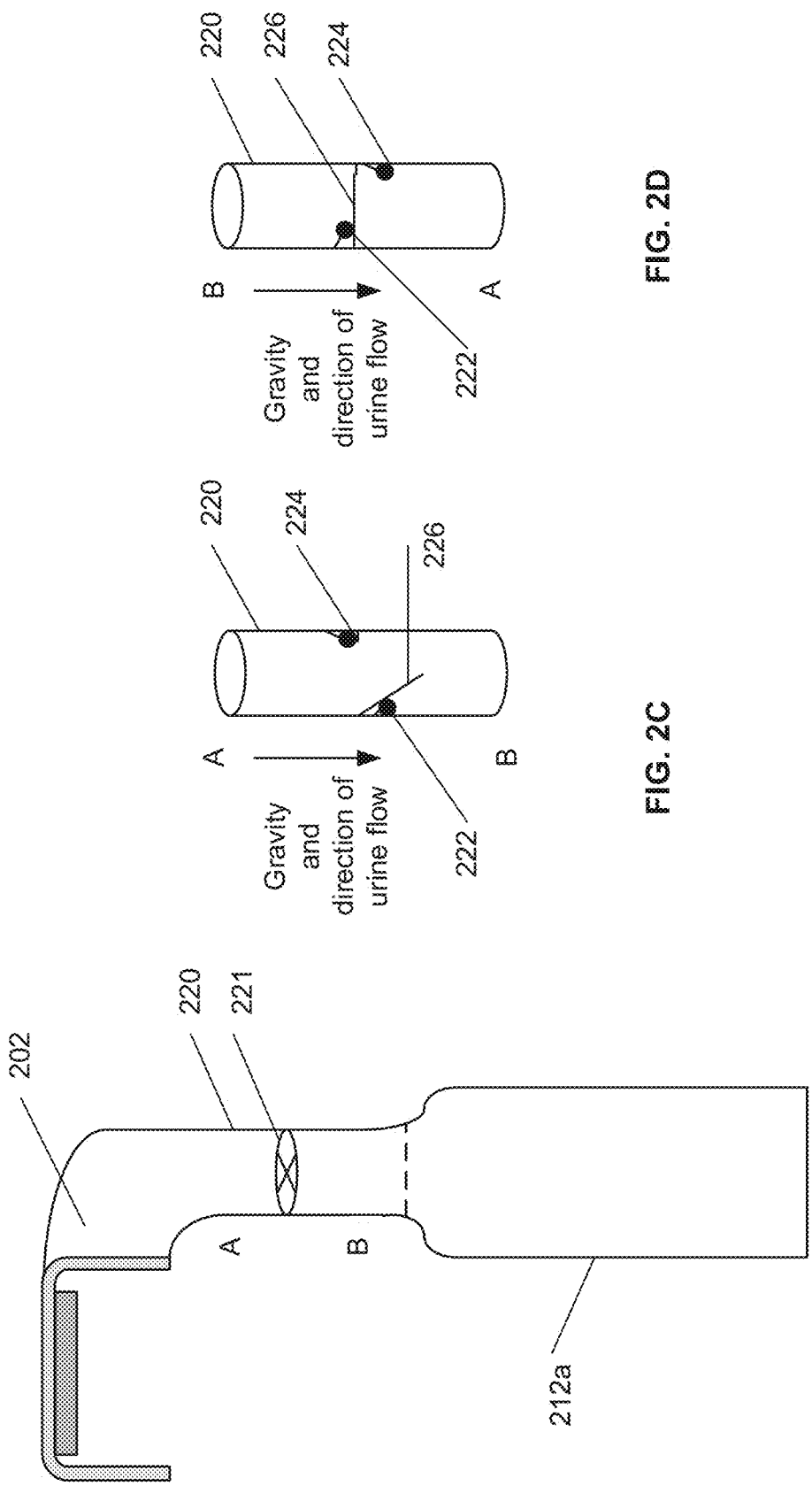

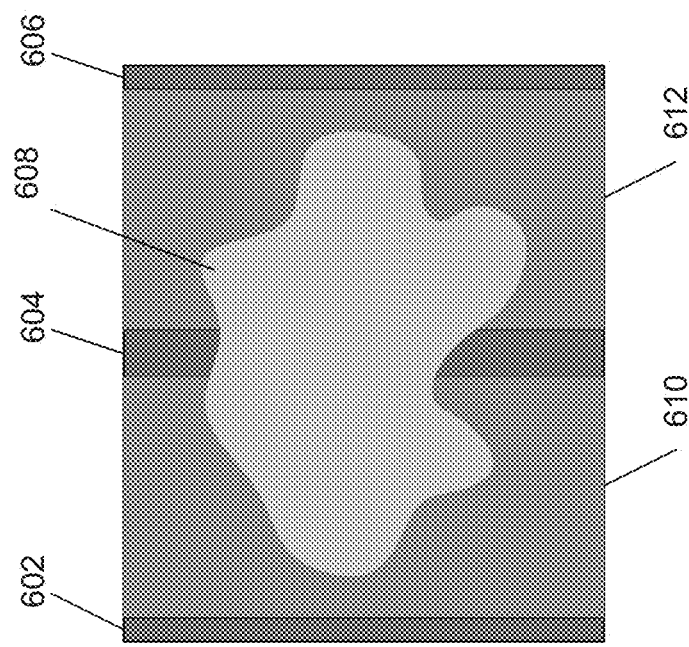
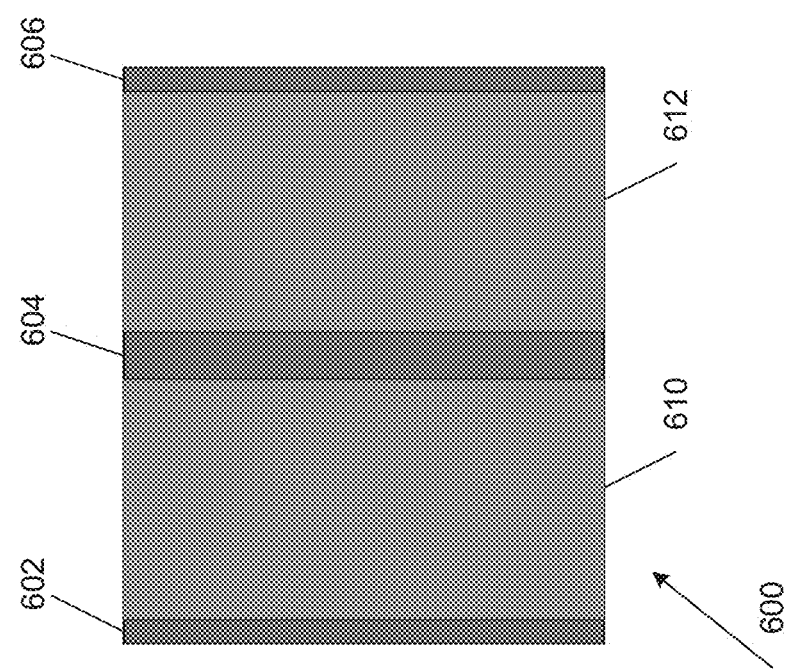
FIG. 6B
FIG. 6A

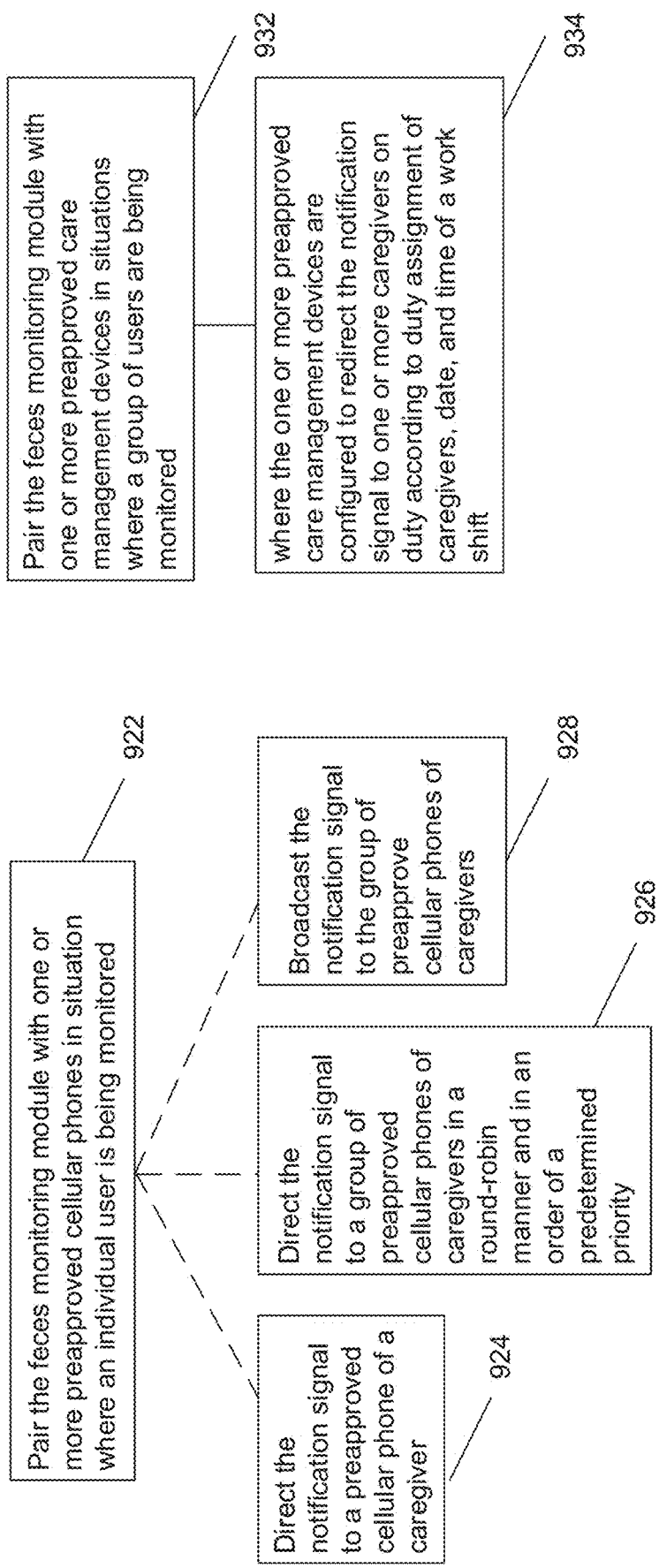

REUSABLE INCONTINENCE UNDERWEAR WITH FECES SENSING

CROSS-REFERENCE TO RELATED APPLICATIONS

This is a continuation-in-part application of U.S. patent application Ser. No. 18/521,183, "Reusable Incontinence Underwear," filed Nov. 28, 2023. The aforementioned United States patent application is assigned to the assignee hereof and are hereby incorporated by reference in its entirety.

FIELD

The present invention relates to the field of incontinence underwear. In particular, the present invention relates to apparatuses of a reusable incontinence underwear with feces sensing and methods for manufacturing the same.

BACKGROUND

An incontinent underwear is an absorbent item used by adults to defecate and urinate without going to the toilet. For people lacking voluntary control over urination or defecation who rely on these incontinent underwear every day, the quality, safety, performance, and environmentally friendly incontinent underwear are paramount. Many types of disposable incontinent underwear are readily available commercially. However, the conventional disposable incontinent underwear suffer from a number of drawbacks, for example: 1) low absorption rate and long absorption time; 2) skin rashes and stains due to contact with urine/feces for a long time; and 3) producing large amount of non-biodegradable waste materials. Therefore, there is a need for an environmentally friendly reusable incontinence underwear that can address the drawbacks of conventional incontinent underwear.

SUMMARY

Apparatuses of reusable incontinent underwear with feces sensing and methods for manufacturing the same are provided. In one embodiment, an incontinence underwear includes an interior layer includes an excretion area, where the excretion area includes one or more openings configured to drain excretions of a user away from the interior layer; a middle layer configured to house an excretion collection unit, configured to store the excretions from the interior layer, and the middle layer further includes a feces sensing unit configured to detect feces discharged from the user; a feces monitoring module electrically coupled to the feces sensing unit, configured to monitor the feces sensing unit and communicate status of the feces sensing unit to one or more caregivers; an exterior layer configured to conceal and prevent leakage from the middle layer of the incontinence underwear; and a support frame configured to hold the interior layer, the middle layer and the exterior layer of the incontinence underwear together.

In another embodiment, a method of manufacturing an incontinent underwear includes forming an interior layer includes an excretion area, where the excretion area includes one or more openings configured to drain excretions of a user away from the interior layer; forming a middle layer configured to house an excretion collection unit, where the excretion collection unit is configured to store the excretions from the interior layer, and where forming the middle layer further includes forming a feces sensing unit configured to detect feces discharged from the user; forming a feces monitoring module electrically coupled to the feces sensing unit, where the feces monitoring module is configured to monitor the feces sensing unit and communicate status of the feces sensing unit to one or more caregivers; forming an exterior layer configured to conceal and prevent leakage from the middle layer of the incontinence underwear; and forming a support frame configured to hold the interior layer, the middle layer and the exterior layer of the incontinence underwear together.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the non-limiting and non-exhaustive aspects of following drawings. The drawings are shown for illustration purposes. They are not drawn to scale. Like numbers are used throughout the specification.

FIG. 2B illustrates an exemplary implementation of urine collection bag according to aspects of the present disclosure.

FIG. 2C illustrates an exemplary valve operation of the urine collection bag of FIG. 2B according to aspects of the present disclosure.

FIG. 2D illustrates another exemplary valve operation of the urine collection bag of FIG. 2B according to aspects of the present disclosure.

FIG. 6A illustrates a top view of an exemplary implementation of a feces sensing unit according to aspects of the present disclosure.

FIG. 6B illustrates the feces sensing unit of FIG. 6A with feces according to aspects of the present disclosure.

FIG. 9D illustrates an exemplary method of pairing a feces monitoring module according to aspects of the present disclosure.

FIG. 9E illustrates another exemplary method of pairing a feces monitoring module according to aspects of the present disclosure.

DESCRIPTION OF EMBODIMENTS

Apparatuses of reusable incontinence underwear with feces sensing and methods for manufacturing the same are provided. The following descriptions are presented to enable a person skilled in the art to make and use the disclosure. Descriptions of specific embodiments and applications are provided only as examples. Various modifications and combinations of the examples described herein will be readily apparent to those skilled in the art, and the general principles defined herein may be applied to other examples and applications without departing from the scope of the disclosure. Thus, the present disclosure is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" is not necessarily to be construed as preferred or advantageous over other aspects or embodiments.

Figure 1:
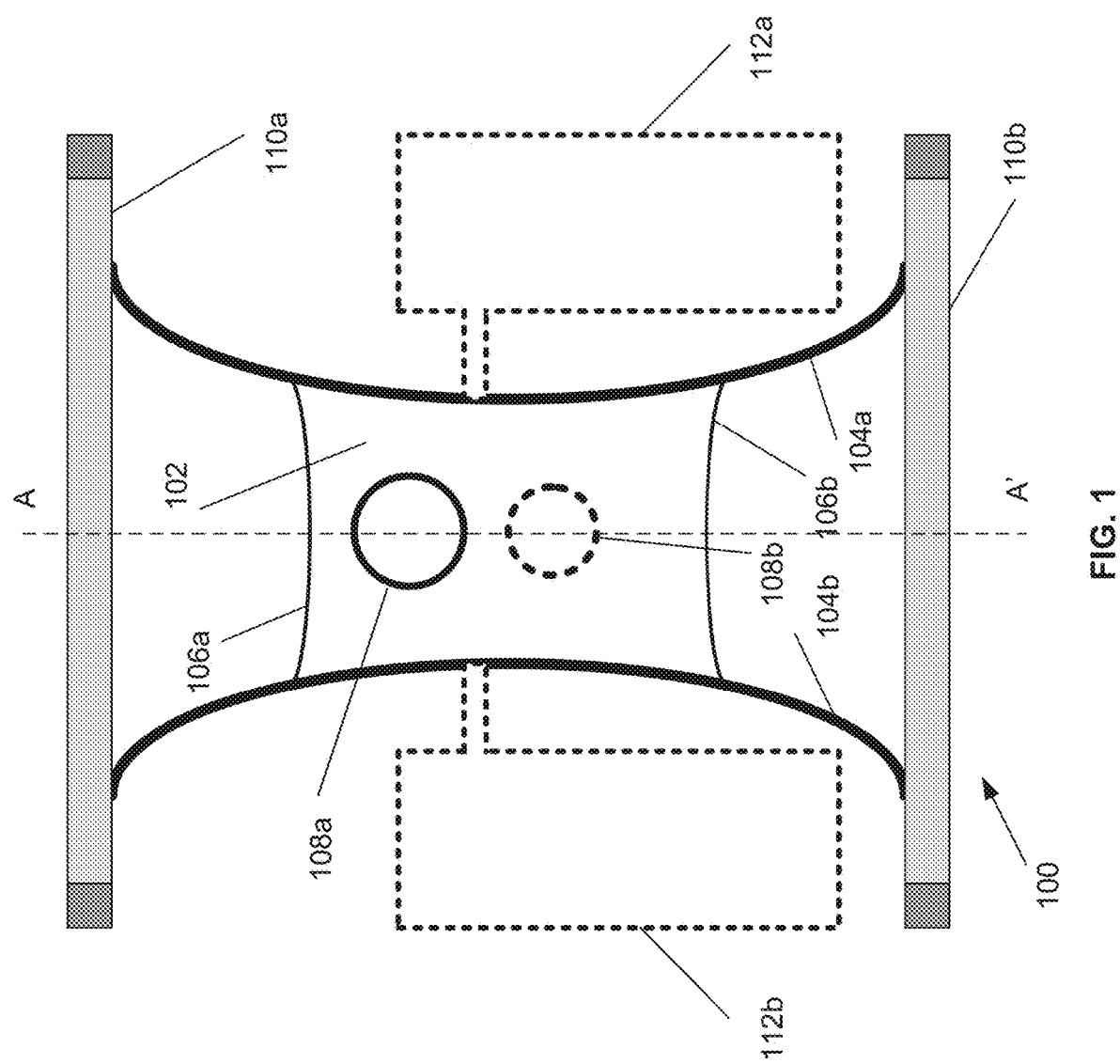
FIG. 1 illustrates a top view of an exemplary reusable incontinence underwear according to aspects of the present disclosure.

FIG. 1 illustrates a top view of an exemplary reusable incontinence underwear according to aspects of the present disclosure. In the example of FIG. 1, a reusable incontinence underwear 100 includes an interior layer 102 and a support frame, represented by lines 104a and 104b. The interior layer includes an excretion area, outlined within the two curve lines 106a and 106b. The excretion area includes opening 108a and may optionally include opening 108b, configured to drain excretions of a user away from the interior layer 102. The interior layer 102 is made of a hydrophobic material configured to repel the excretions of the user to the middle layer of the incontinence underwear. The reusable incontinence underwear 100 may include strapping mechanisms, represented by 110a and 110b, configured to strap the reusable incontinence underwear to the body of a user. The reusable incontinence underwear 100 may further include one or more external urine collection bags, represented by 112a and 112b, configured to store urine from the user.

According to aspects of the present disclosure, the interior layer 102 can be made of a silicone coated cotton-lycra fabric, a breathable, stretchable polytetrafluoroethylene treated cotton-spandex waterproof fabric sheet or polytetrafluoroethylene treated nylon-spandex waterproof fabric sheet. The interior layer is attached to the support frame. The upper surface of the interior layer is configured to closely contact with the skin of a user to avoid skin rashes and stains from urine and feces. The lower surface, also referred to as the excretion area, of the interior layer is configured to adhere with an excretion collection unit.

Figure 2A:
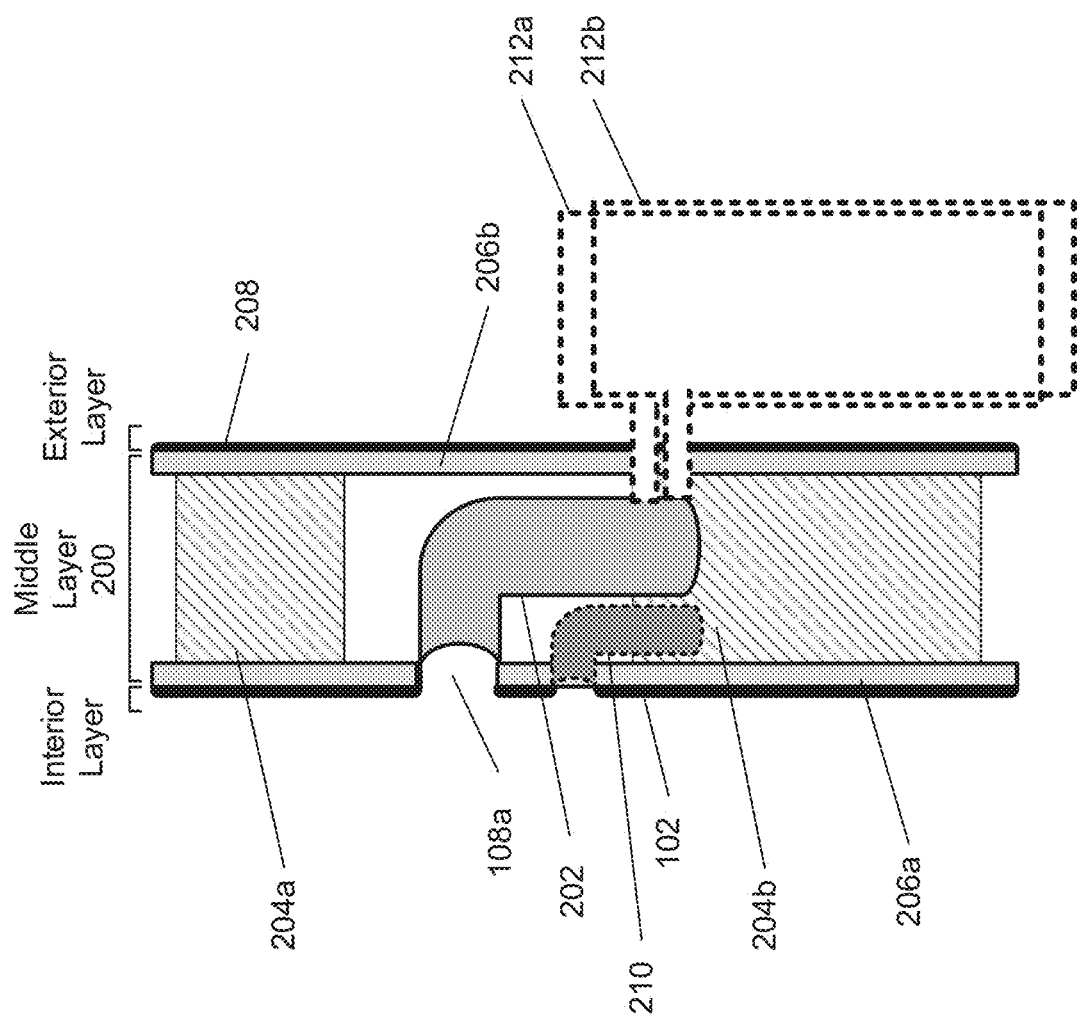
FIG. 2A illustrates a cross sectional view of the exemplary reusable incontinence underwear of FIG. 1 according to aspects of the present disclosure.

FIG. 2A illustrates a cross sectional view of the exemplary reusable incontinence underwear of FIG. 1 according to aspects of the present disclosure. The cross sectional view may be envisioned as a view along line AA' (shown in FIG. 1) of the exemplary reusable incontinence underwear 100. In the example shown in FIG. 2A, a middle layer 200 is configured to house an excretion collection unit, where the excretion collection unit is configured to store the excretions from the interior layer. The excretion collection unit includes a urine collection unit having a urine guide 202 configured to drain urine away from the interior layer to one or more urine absorbent pads, represented by 204a and 204b in the middle layer 200. The urine collection unit further includes a urine transfer pouch 206 made of a hydrophilic fabric and is configured to accelerate urine absorption by spreading and transferring urine to the one or more urine absorbent pads 204a and 204b.

As shown in FIG. 2A, a urine transfer pouch, represented by 206a and 206b, is attached to interior layer 102 and exterior layer 208, respectively. The urine transfer pouch may transfer the remaining urine to the urine absorbent pads 204a and 204b. According to aspects of the present disclosure, the exterior layer 208 is configured to conceal and prevent leakage from the middle layer, labelled as 200, of the reusable incontinence underwear. The exterior layer 208 is made of a breathable material configured to allow moisture from the middle layer to escape the incontinence underwear.

According to aspects of the present disclosure, a urine guide 202 can be made of a 2 mm thick flexible high density polyethylene sheet, where the upper surface of the urine guide may attach around the urine opening of the interior layer. Both sides of the urine guide are attached to the inner surface of the support frame, configured to provide a space to facilitate transfer of urine away from the genital to the urine collection bags. In some applications, the urine guide may drain about 90% to 95% urine output away from the genital during urination. The front portion of the urine guide is attached to the urinary opening of the interior layer, where the front rim of the urine guide may be in close contact with the urinary opening around the genital to prevent urine leakage. Based on the size of the incontinence underwear, the size of the urine guide may be 1 cm to 2.5 cm in height and 3 cm to 5 cm in width, configured to provide enough room to cover the genital.

In some implementations, the front portion of the urine guide 202 may be attached to the urinary opening of the interior layer, configured to drain about 90% to 95% of urine output away from the genital. The inner surface of the urine guide may be covered with a 3 mm thick middle microfiber pad such as a striped urine guiding pad, which may be made of a polytetrafluoroethylene coated microfiber non-woven fabric. The striped urine guiding pad can further function to guide urine flow away from the genital area down the urine guide and spread the remaining 5% to 10% urine into the rear urine transfer pad 206b. According to aspects of the present disclosure, the incontinence underwear may optionally include a feces collection unit. The feces collection unit includes a feces collection bag 210. The feces collection unit can be washable. A used feces collection bag can be replaced with a new feces collection bag.

In some implementations, the urine collection unit is configured to drain majority of urine away from the interior layer to one or more urine collection bags, shown as 212a and 212b, via a valve controlled conduit; and the urine guide can be further configured to drain remaining urine away from the interior layer to one or more urine absorbent pads in the middle layer.

In some implementations, the feces collection unit may optionally and/or additionally include a barrier anus mount (not shown) with air cushion rectum seat in the central portion. The barrier anus mount may be made of thermoplastic elastomers or polydimethylsiloxane rubber sheet with a dimension of 3 cm to 4 cm in width which may have the same distance between the inner surface of the support frames 104a and 104b. The height of the barrier anus mount may be the same height of the support frame and with a length of 5 cm to 6 cm. The barrier anus mount may be attached around the fecal drain opening of the interior layer as well as to the inner surface of the support frames 104a and 104b. The barrier anus mount can function to block urine flow from reaching anus.

The barrier anus mount includes an air cushion rectum seat bonded on the top of a feces drain opening, which may be located at the central portion of the barrier anus mount. The air cushion rectum seat may be snug fitted to the rim of the rectum, allowing collection of feces. The feces collection bag may be detachable from the rectum air cushion seat, allowing changing or disposing of a used feces collection bag. The feces collection bag of the present disclosure is distinguished from the conventional incontinence underwear. With conventional incontinence underwear that collect feces directly on the inner layer of the incontinence underwear, which may cause feces to stain the skin or genital of the user, causing rashes to the skin or genital of the user.

According to aspects of the present disclosure, the exterior layer 208 may be made of a stretchable, breathable, washable polyurethane coated polyester spandex waterproof fabric sheet or polytetrafluoroethylene treated cotton-spandex waterproof fabric sheet or polytetrafluoroethylene treated nylon-spandex waterproof fabric sheet. In some implementations, the urine transfer pouch can be made of a hydrophilic wicking material, such as hydrophilic microfiber non-woven fabric.

The urine transfer pouch includes a front double layer microfiber pad, a middle vertical striped microfiber pad and a rear double layer microfiber pad. The front and the rear double layer microfiber pads can be made of one piece of 6 cm×14 cm×2 mm microfiber non-woven fabric sheet.

FIG. 2B illustrates an exemplary implementation of urine collection bag according to aspects of the present disclosure. In the example shown in FIG. 2B, a urine collection bag 212a can be coupled to the urine collection unit 202 for storing urine from a user. The urine guide may be setup to transfer about 90% to 95% of urine output away from the external genitalia, and urine output may move downward to the urine ports which are located at support frame 104a and 104b above the upper surface of the barrier anus mount. Then, urine flows through a valve 221 controlled urine conduit 220 into one or more urine collection bags, shown as 212a and 212b.

According to aspects of the present disclosure, the urine collection bag 212a may be detached from the urine collection unit 202 for cleaning and sterilization. Different sizes of urine collection bag may be used, for example a 250 ml bag or a 500 ml bag, depending on duration of usage and specific user requirements. In addition, multiple urine storage bags may be used, for example one strapped to the left tight and one strapped to the right tight of the user, depending on duration of usage and specific user requirements.

FIG. 2C illustrates an exemplary valve operation of the urine collection bag of FIG. 2B according to aspects of the present disclosure. In the example of FIG. 2C, points A and B correspond to points A and B in FIG. 2B. In the case of FIG. 2C, gravity and direction of urine flow goes from point A to point B. In this case, the weight of the urine and the balls 222 and 224 pull a cover 226 of the valve 221 to open, allowing urine to flow from point A to point B and into the urine collection bag 212a.

FIG. 2D illustrates another exemplary valve operation of the urine collection bag of FIG. 2B according to aspects of the present disclosure. Similar to the example of FIG. 2C, points A and B correspond to points A and B in FIG. 2B. In the case of FIG. 2D, gravity and direction of urine flow goes from point B to point A, for example the user may be upside down or the urine collection bag 212a may be in a position higher than the urine collection unit 202. In this case, the weight of the urine and the balls 222 and 224 push the cover 226 of the valve 221 to close, preventing urine to flow from point B to point A and back to the user.

Figure 3B:
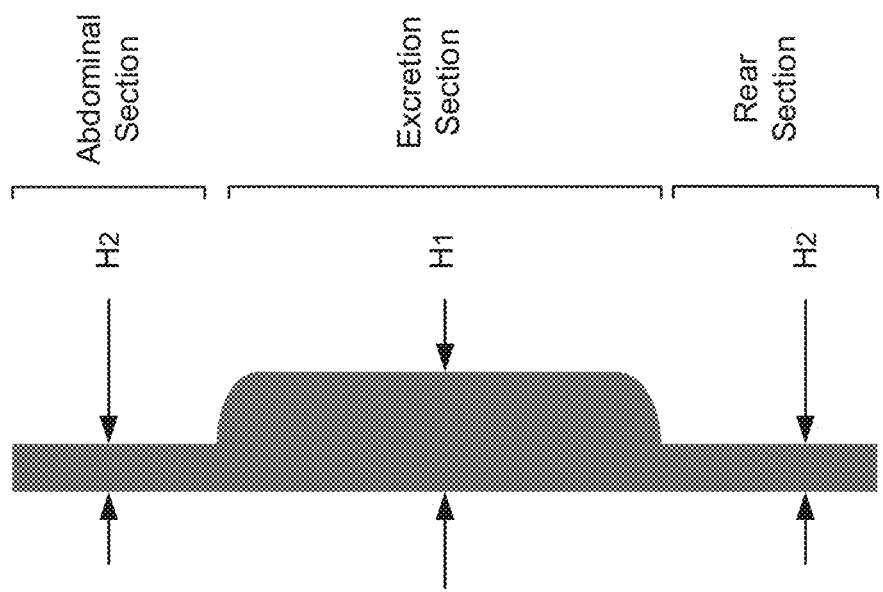
FIG. 3B illustrates a side view of the support frame of FIG. 3A according to aspects of the present disclosure.
Figure 3A:
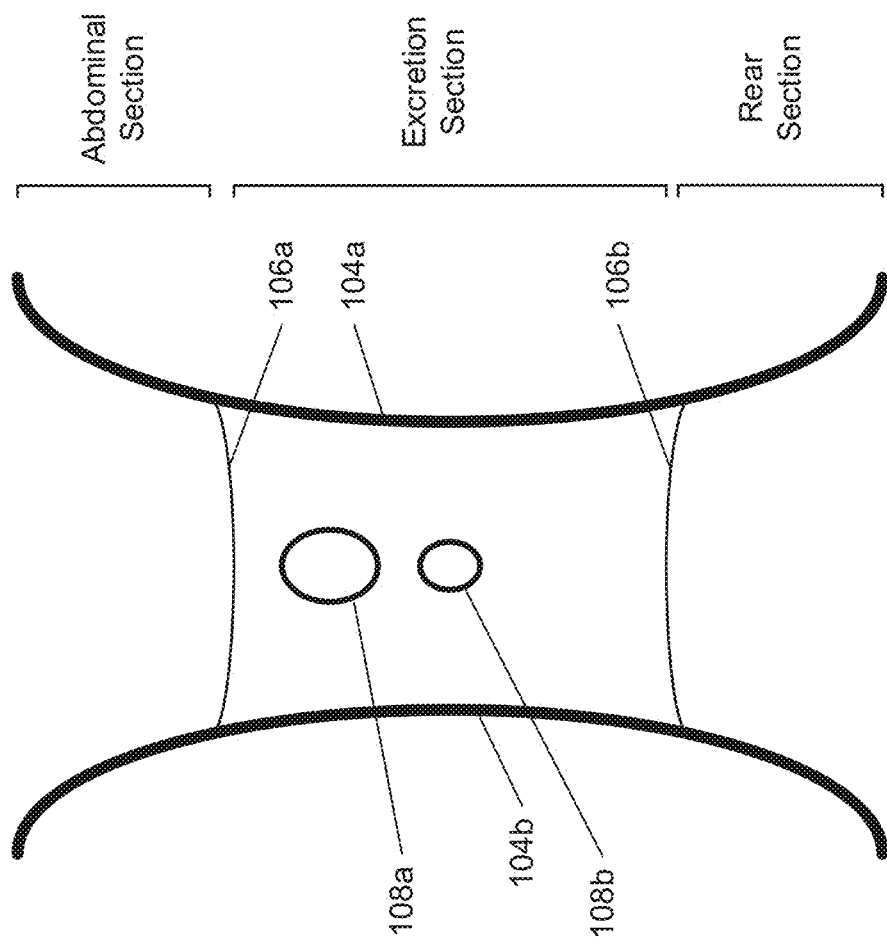
FIG. 3A illustrates a top view of an exemplary implementation of a support frame of the exemplary reusable incontinence underwear of FIG. 1 according to aspects of the present disclosure.

FIG. 3A illustrates a top view of an exemplary implementation of a support frame of the exemplary reusable incontinence underwear of FIG. 1 according to aspects of the present disclosure. Some of the components shown in FIG. 3A are the same as the components shown in FIG. 1. The description of similar components are not repeated here. As shown in the example of FIG. 3A, the support frame includes an excretion section located around the genital area of the user configured to hold the excretion collection unit, an abdominal section of the support frame located at a front portion of the crotch area configured to hold the incontinence underwear that touches an abdominal area of the user, and a rear section of the support frame located at a back portion of the crotch area configured to hold the incontinence underwear that touches a rear area of the user.

According to aspects of the present disclosure, the support frame is configured to hold the interior layer, the middle layer and the exterior layer of the incontinence underwear together. The support frame is made of hydrophobic polydimethylsiloxane rubber or thermoplastic elastomers, and is configured to wrap around the crotch area of the user to prevent leakage.

FIG. 3B illustrates a side view of the support frame of FIG. 3A according to aspects of the present disclosure. As shown in FIG. 3B, the support frame in the excretion section has a height of $H_1$. The height of $H_1$ depends on different sizes for different users, which may have a range of 2 to 3.5 centimeters. The support frame in the abdominal and rear sections have a height of $H_2$. The height of $H_2$ depends on different sizes for different users, which may have a range of 0.8 to 1.2 centimeters.

According to aspects of the present disclosure, the increased height of the support frame in the excretion area is designed to seal the incontinence underwear to the crotch area of the user and to provide an air gap between the excretion area of the interior layer of the incontinence underwear and a genital area of the user. The air gap reduces or prevents feces from touching the skin of the user. The height of the support frame in the abdominal and rear sections are designed to have a lower height than the excretion area, which allows a close snug to the skin of the user in the abdominal and rear areas of the incontinence underwear.

According to aspects of the present disclosure, the incontinence underwear is configured to fold or unfold in a first direction to provide access to the excretion collection unit in the middle layer of the incontinence underwear; and where the incontinence underwear is further configured to fold or unfold in a second direction to wrap or unwrap the incontinence underwear around the crotch area of the user.

Figure 3C:
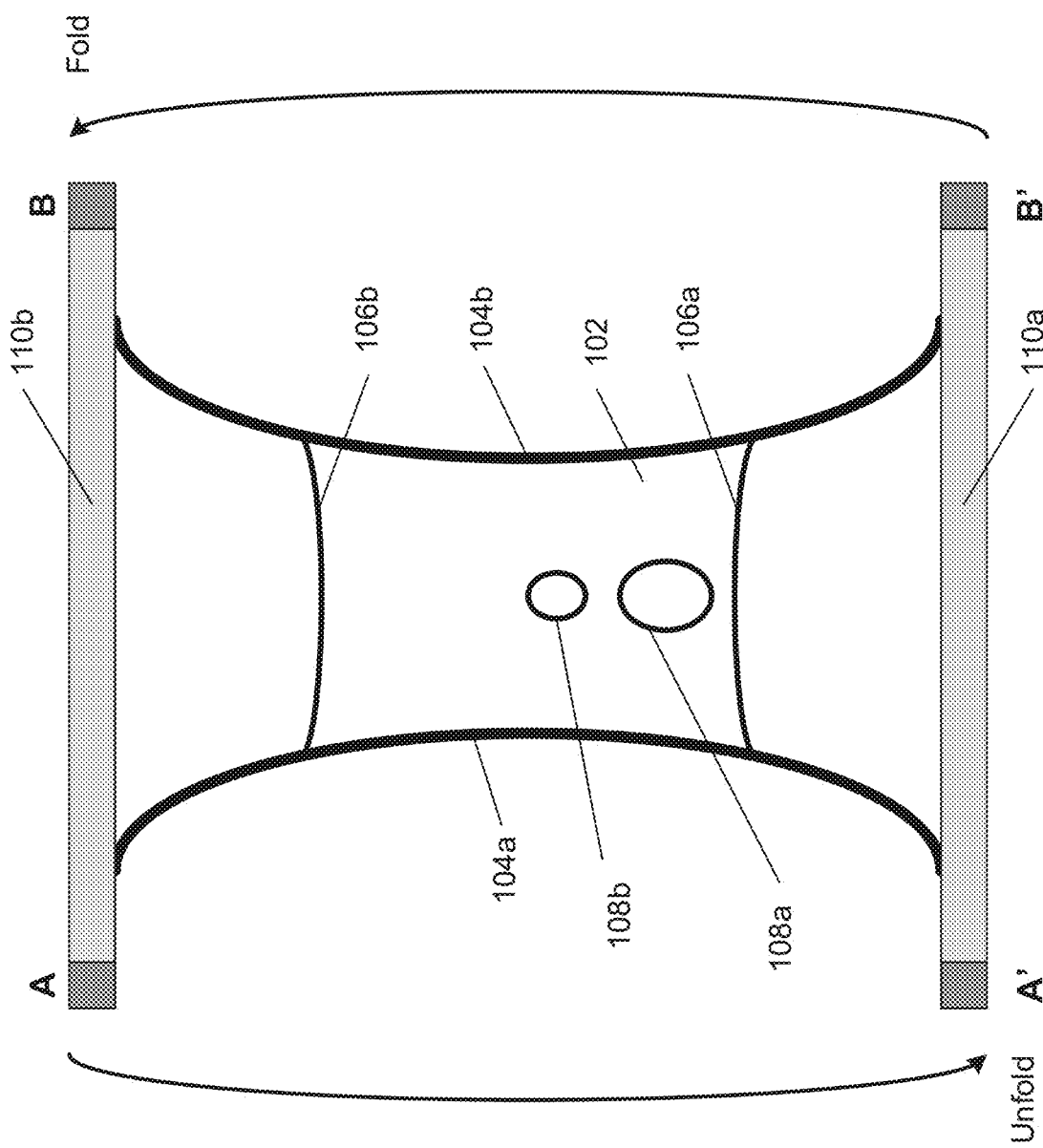
FIG. 3C illustrates an exemplary implementation of fold and unfold operations of the exemplary reusable incontinence underwear of FIG. 1 according to aspects of the present disclosure.

FIG. 3C illustrates an exemplary implementation of fold and unfold operations of the exemplary reusable incontinence underwear of FIG. 1 according to aspects of the present disclosure. The fold and unfold operations are performed by closing and opening the incontinence underwear by moving the strapping mechanism 110a with point A and point B at each end, and the strapping mechanism 110b with point A' and point B' at each end.

In FIG. 3C, the incontinence underwear is shown in an unfold position, ready to be worn by a user. The incontinence underwear may be folded by attaching point A' to point A and point B' to point B. On the other hand, the incontinence underwear may be unfolded by detaching point A' from point A and point B' from point B. According to aspects of the present disclosure, the strapping mechanism may be implemented by various means, for example using magnetic strips, adhesive strips, Velcro strips, and etc.

Figure 3D:
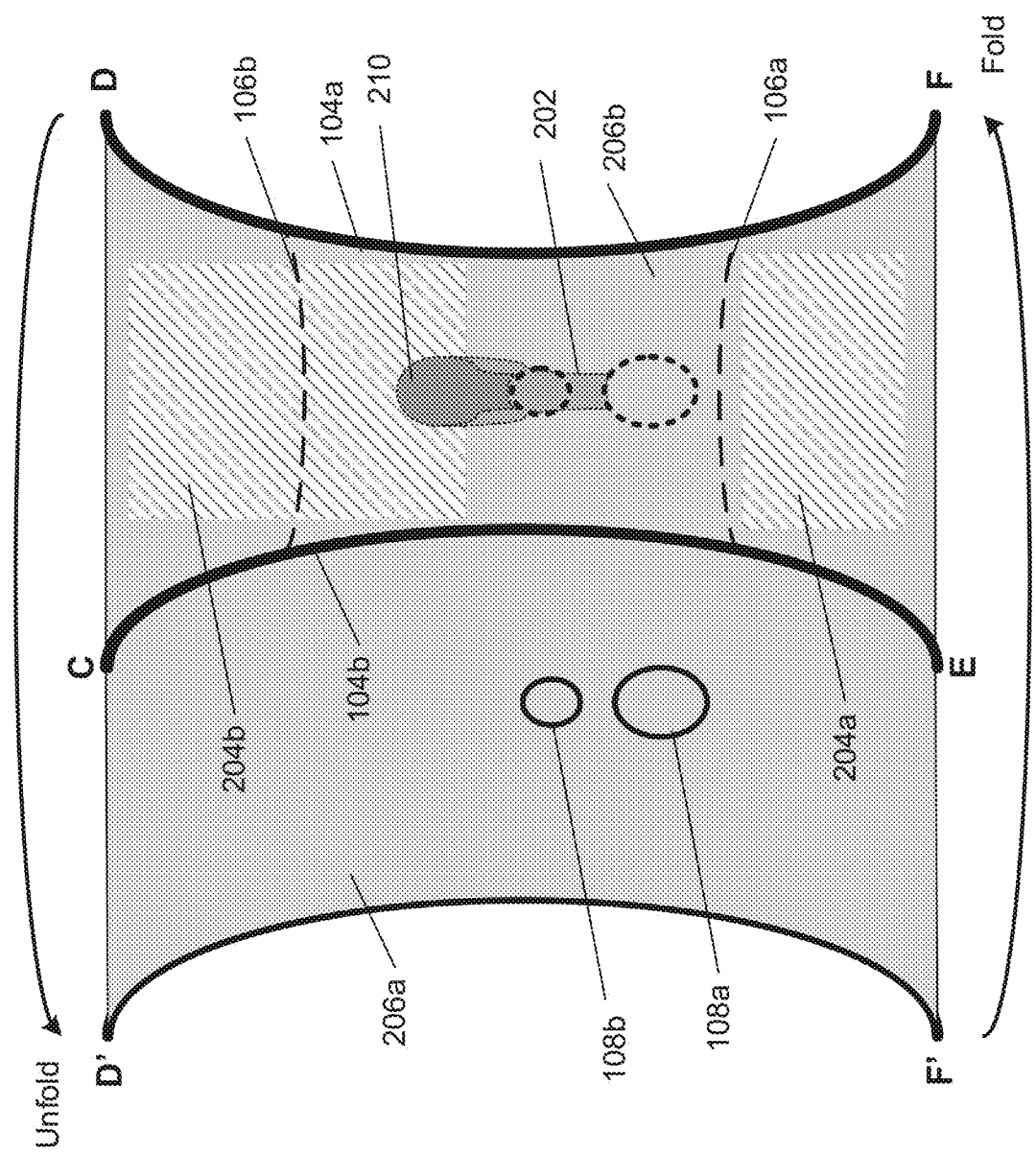
FIG. 3D illustrates another exemplary implementation of fold and unfold operations of the exemplary reusable incontinence underwear of FIG. 1 according to aspects of the present disclosure.

FIG. 3D illustrates another exemplary implementation of fold and unfold operations of the exemplary reusable incontinence underwear of FIG. 1 according to aspects of the present disclosure. Some of the components shown in FIG. 3A are the same as the components shown in FIG. 1. The description of similar components are not repeated here.

As shown in FIG. 3D, the incontinence underwear may be folded and unfolded to provide access to the middle layer of the reusable incontinence underwear for activating the hydrophobic drying pouch or changing the urine absorbent pads. In this exemplary implementation, the right hand side of the support frame 104a along with the interior layer may be configured to be detachable along the curve line DF. In the unfold form, the left hand side of the support frame 104b remains along the curve line CE, while the right hand side of the support frame 104a along with the interior layer is moved to the curve line D'F'. In the unfold form, the urine absorbent pads 204a and 204b may be changed; the urine collection unit 202 and the feces collection unit 210 may be replaced; and the middle layer of the incontinence underwear may be cleaned. After accessing the middle layer, the incontinence underwear may be folded by moving the right hand side of the support frame 104a along with the interior layer back to its original position, i.e. curve D'F' is folded back to curve DF.

Note the directions of the fold and unfold operations in FIG. 3D are shown for illustration purposes. In other embodiments, the left hand side of the support frame 104b along with the interior layer may be configured to be detachable along the curve line CE (not shown). According to aspects of the present disclosure, the folding and unfolding mechanism may be implemented by various means, for example using magnetic strips, adhesive strips, Velcro strips, and etc.

In some implementations, the top layer of the front double layer microfiber pad 206a can be adhered on the inner surface of the interior layer in the abdomen portion, where one or more pieces of urine absorbent pads 204a can be placed on the inner surface of the top layer of the front double layer microfiber pad. The bottom layer of the front double layer microfiber pad can be adhered on the exterior layer. When the interior layer is folded horizontally, the inner layer of the incontinence underwear can be configured to hold the urine absorbent pad 204a, which is sandwiched between the top layer and the bottom layer of the front urine transfer pouch. In addition, when the interior layer is unfolded from the inner layer of the incontinence underwear to open the front double layer microfiber pad, access is provided to the reusable components of the incontinence underwear, and allows used urine absorbent pads to be changed.

Similarly, the top layer of the rear double layer microfiber pad 206b can be adhered on the inner surface of the interior layer in the top buttocks portion and the bottom layer of the rear double layer microfiber pad can be adhered on the inner surface of the exterior layer, where one or more pieces of urine absorbent pad 204b can be placed on the surface of the inner layer. When the interior layer is folded horizontally, the inner layer of the incontinence underwear can be configured to hold the urine absorbent pad 204b, which is sandwiched between the top layer and the bottom layer of the rear double layer microfiber pad. In addition, when the interior layer is unfolded horizontally from the inner layer of the incontinence underwear to open the rear double layer microfiber pad, access is provided to the reusable components of the incontinence underwear, and allows used urine absorbent pads to be changed.

Figure 4B:
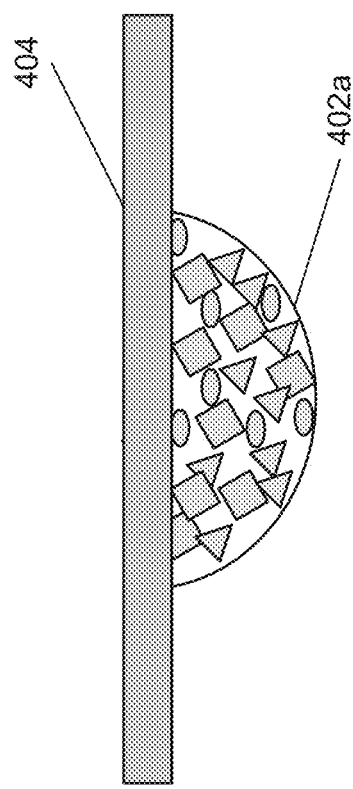
FIG. 4B illustrates an exemplary implementation of a collection cup of the urine absorbent pad of FIG. 4A according to aspects of the present disclosure.
Figure 4A:
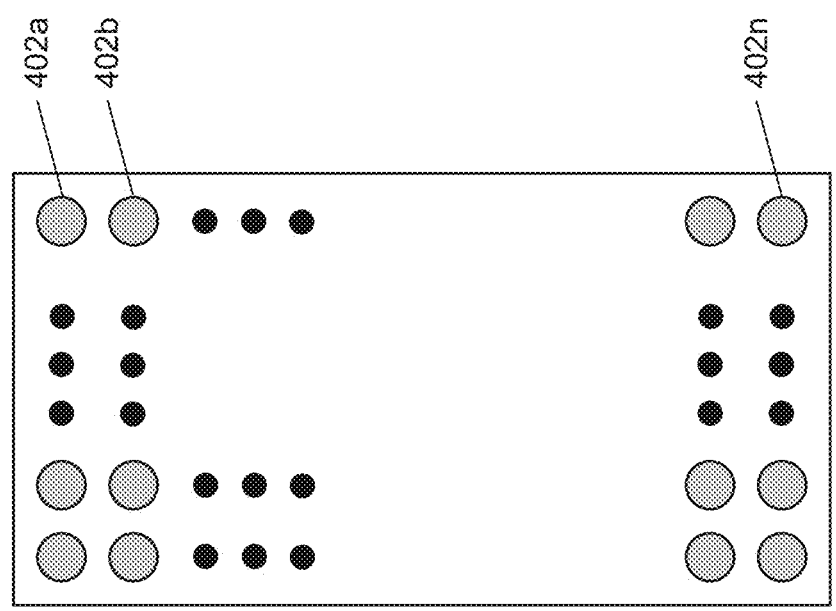
FIG. 4A illustrates an exemplary implementation of a urine absorbent pad according to aspects of the present disclosure.

FIG. 4A illustrates an exemplary implementation of a urine absorbent pad according to aspects of the present disclosure. FIG. 4B illustrates an exemplary implementation of a collection cup of the urine absorbent pad of FIG. 4A according to aspects of the present disclosure. In this exemplary implementation, a urine absorbent pad 400 may include a group of collection cups (represented by 402a, 402b . . . 402n, etc.) connected with a carboxymethyl cellulose (CMC) paper sheet 404. Each cup, for example 402a, in the group of collection cups can be configured to hold biodegradable superabsorbent polymer particles and toilet paper scraps for absorbing urine from the user.

According to aspects of the present disclosure, a used urine absorbent pad is flushable in a toilet. Based on the size of the user and other application criteria, various sizes of urine absorbent pad may be designed. In one implementation, a urine absorbent pad having a rectangular shape of approximately 2 cm to 3 cm in width and 10 cm to 14 cm in length may be used to fit the drainage of a toilet. In some embodiments, a reusable incontinence underwear may be designed to hold multiple urine absorbent pads for situations where it is desirable to prolong the period of changing the incontinence underwear and/or changing the urine absorbent pads.

According to aspects of the present disclosure, the urine absorbent pad is designed with the following features, including but not limited to: 1) use a flushable, dispersible and biodegradable CMC paper; 2) supported by the urine transfer pouch and the support frame to provide space for the superabsorbent polymer particles to undergo free swelling process in order to maximize urine absorption capacity; 3) provide a uniform distribution of 2 grams to 3 grams biodegradable super absorbent polymer particles in the group of collection cups of the urine absorbent pad; 4) use two or more urine absorbent pads in the urine collection unit for an extended period of time without changing the urine absorbent pads; 5) sandwich the urine absorbent pads between the top layer and the bottom layer of the microfiber pads of the urine transfer pouch to provide tensile strength; and 6) enable a used urine absorbent pad to disintegrate in toilet water. According to aspects of the present disclosure, the urine absorbent pad uses collection cups to achieve desirable urine swelling rate and swelling capacity. One advantage of the disclosed urine absorbent pad is that it can be disintegrated in water, allowing used urine absorbent pad to be flushed in a toilet.

In some implementations, based on the size and intended duration of use of the incontinence underwear, the main structure of a urine absorbent pad may include 6 to 20 collection cups as the SAP particles holder, for example in 10×1, 10×2, 6×1, 6×2, and 6×3 configurations. In the example of 10×1 configuration, the urine absorbent pad may have a dimension of 12 cm×2.5 cm×0.8 cm, where the collection cups may be made by mixing appropriate proportions of CMC powder, wood fibers and room temperature water-soluble polyvinyl alcohol into pulp and hot-press pulp into a urine absorbent pad with 6 to 20 collection cups.

In some implementations the urine absorbent pad includes a muffin pan shaped superabsorbent polymer (SAP) holder which is made of paper pulp by mixing 0.5 weight % to 1.2 weight % of biodegradable hydrophilic carboxymethyl cellulose (CMC), 20 weight % to 30 weight % of hardwood and softwood blend fibers, 2 weight % to 3 weight % of room temperature water soluble polyvinyl alcohol and water into paper pulp and then hot press pulp into muffin pan shaped SAP holder and carboxymethyl cellulose paper sheet. The addition of CMC into paper pulp can increase the dry and wet strength, wicking and absorbance properties of the SAP holder for making a urine absorbent pad. The muffin pan shaped SAP holder has 6 to 20 collection cups to uniformly distribute the superabsorbent particles into each collection cup of the urine absorbent pad, for example 10×1, 10×2, 6×1 and 6×2 configurations. In the example of 10×1 configuration, the urine absorbent pad 12 cm×2.5 cm×0.8 cm may contain 2 grams to 3 grams of superabsorbent polymer particles.

In some implementations, the SAP holder may include 6 to 24 collection cups, such as 6×1 matrix; 6×2 matrix; 6×3 matrix and 6×4 matrix; for example a 6×1 matrix urine absorbent pad with a dimension of 14 cm×2.5 cm×1 cm urine absorbent pan with 6 collection cups, where each round shaped collection cup has a 2 cm in diameter and 1 cm in depth with a total volume of 19 ml and a thin flushable CMC paper mesh sheet as the cover of the collection cups. A mixture of 2 ply toilet paper scraps and biodegradable superabsorbent polymer particles may put into each collection cup which may contain 200 mg to 400 mg of biodegradable superabsorbent polymer particles, and then the water-soluble pressure-sensitive adhesive is used to seal the collection cups with a thin flushable CMC paper mesh sheet to form an flushable urine absorbent pad with a dimension of 14 cm×2.5 cm×1 cm, which may contain 1.2 g to 2.4 g superabsorbent polymer particles. The benefit of mixing the biodegradable superabsorbent polymer particles with the two ply toilet paper scraps is to use wicking toilet paper to quickly hold urine, which in turn allows the biodegradable superabsorbent particles time to absorb urine and dry out the toilet paper for the next wave of urine absorption. The function of the urine collection cups is to provide enough room required for the expansion when wetted biodegradable superabsorbent polymer particles are under free swelling to provide an optimal urine absorption capacity for drying the genital area and preventing rashes.

Each cup can be filled with a mixture of dry two ply toilet paper scraps and about 200 mg to 400 mg of biodegradable superabsorbent polymer particles, then put another 2 mm thick two ply toilet paper sheet on the top of the mixture of two ply toilet paper scraps and biodegradable superabsorbent polymer particles and then put a 2 mm thick flushable CMC paper cover on the top of the cups, and then the water-soluble pressure-sensitive adhesive is used to seal the cups with the flushable CMC paper cover to form a 14 cm×2.5 cm×1 cm urine absorbent pad. This method of sandwiching the biodegradable superabsorbent polymer particles between two ply toilet paper scraps is to use toilet paper absorb urine to provide the biodegradable superabsorbent particles having time to absorb urine and dry out the toilet paper for the next round of urine absorption. The collection cups are configured to provide room required for the expansion of wetted biodegradable superabsorbent polymer particles. The biodegradable superabsorbent polymer particles in the urine absorbent pad are under free swelling to have an optimal urine absorption capacity, which in turn keeps the genital area drying and prevents rashes to the skin of the user. In some other implementations, several of the urine absorbent pads may be used together according to the actual urine absorption needs or desired duration between incontinence underwear changes.

For example 10×2 configuration urine absorbent pad may include two parallel pieces of 10×1 configuration 12 cm×2.5 cm×8 mm urine absorbent pads, which may be formed on the top surface of a room temperature water-soluble polyvinyl alcohol film, then a water soluble polyvinyl alcohol pressure sensitive adhesive may be used to bond two parallel pieces of 12 cm×2.5 cm×8 mm urine pads together to form a 12 cm×5 cm×8 mm urine absorbent pad.

Another feature of the urine absorbent pad is that several 6×1 matrix of 14 cm×2.5 cm×1 mm urine absorbent pads may be arranged together according to the actual urine absorption needs. For example, a 6×3 matrix flushable urine absorbent pad can include three parallel pieces of 14 cm×2.5 cm×1 cm flushable urine absorbent pads which are placed on the top surface of a room temperature water soluble polyvinyl alcohol film which is coated with a thin layer of water soluble polyvinyl alcohol pressure sensitive adhesive on the surface is used to bond the three parallel pieces of 14 cm×2.5 cm×1 cm flushable urine pads together to form a 14 cm×7.5 cm×1 cm urine absorbent napkin which may contain 3.6 g to 7.2 g superabsorbent polymer particles and has a total urine absorption capacity of 170 to 340 ml (47 ml/g×3.6 g=169.2 ml).

Based on experimental data, a normal urine output of a user may depend on age, weight, and health. An average urine output of a senior user is about 1.0 ml/kg/hr. Assume every 4 hours a senior user may have one times urinary and the user who weigh 65 kg may have a urine output about 260 ml for 4 hours duration (1.0×65 kg×4 hrs.=260 ml). According to the experimental results of one commercial SAP sample, the absorption under load (AUL) equilibrium absorption capacity of SAP in the saline solution is about 19.04 ml urine/g SAP. Thus, it may need about 14 grams of SAP particles (260 ml/19.04 ml/g SAP=19 grams) to absorb 260 ml of urine output. An exemplary implementation of the disclosed incontinence underwear contains 2.4 to 4.8 grams of SAP.

Figure 4C:
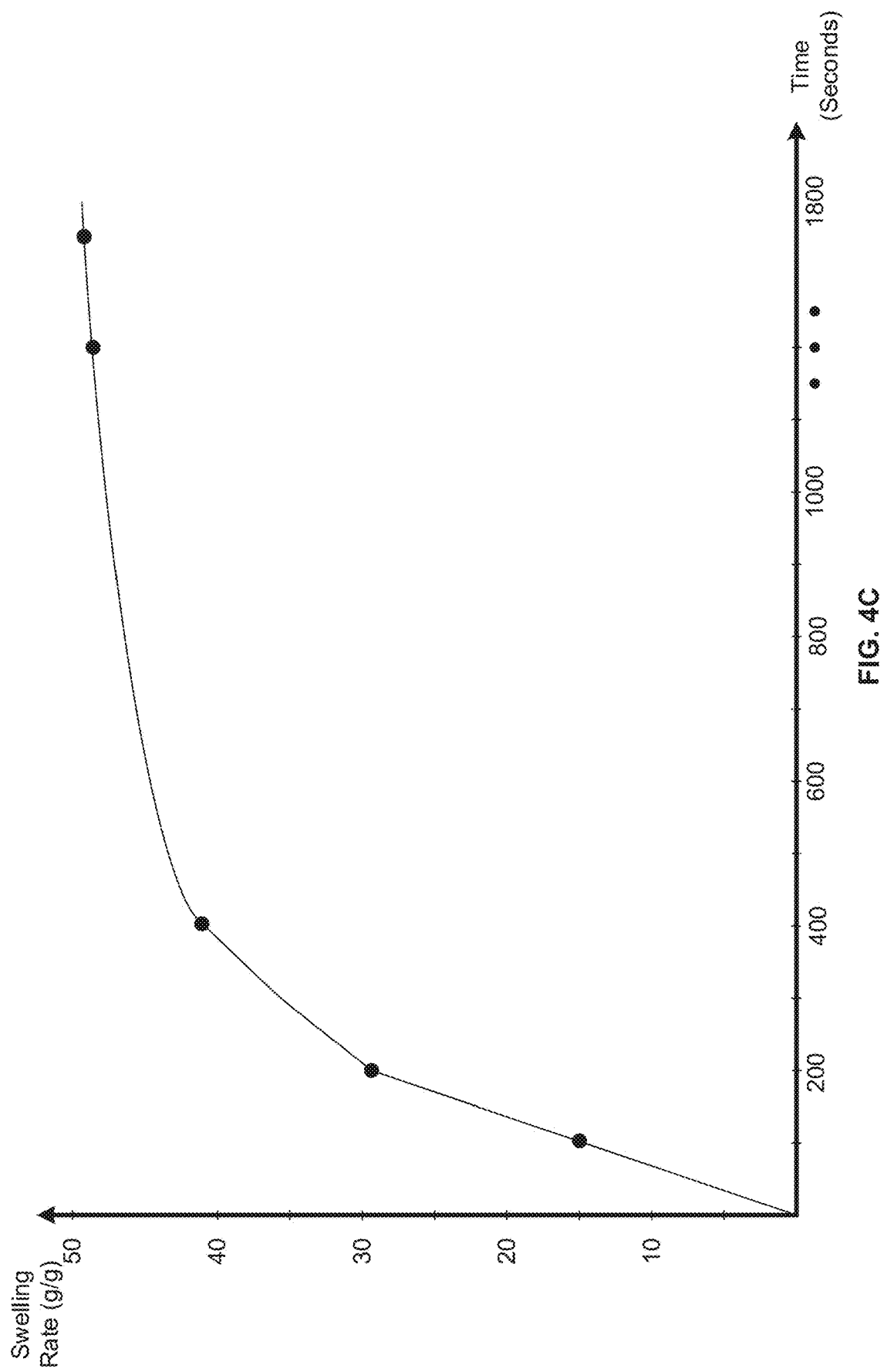
FIG. 4C illustrates an exemplary graphical representation of the swelling rate of superabsorbent polymer particles in a urine solution according to aspects of the present disclosure.

The kinetics of the superabsorbent polymer (SAP) swelling process can be used to analyze how long it should take for an incontinence underwear to absorb this 36 ml of urine output. The kinetics of the SAP swelling can be described mathematically using empirical models, such as Voigt viscoelasticity model. FIG. 4C illustrates an exemplary graphical representation of the swelling rate of superabsorbent polymer particles in a urine solution according to aspects of the present disclosure. In the example of FIG. 4C, the swelling rate (also referred to as absorption rate) of a commercial SAP particles sample in a synthetic urine solution (NaCl 0.9 weight % or 0.279 mole %) under free swelling condition without loading pressure as a function of time can be expressed by the Voigt equation:

$$A_t = A\infty(1-\exp(-t/T))$$

where $A_t$ represents (g/g) absorption at time t; $A\infty$ (g/g) represents the power parameter (g urine/g SAP), indicating the theoretical equilibrium of urine absorption; t(s) represents absorption time; and T(s) is the rate parameter, representing the relaxation time required to reach 0.632 of equilibrium urine absorption.

At (ml salt solution/g SAP)=0.632 $A\infty$ at the retardation time

At (ml salt solution/g SAP) vs absorption time has a linear relationship $dA_t/dt$=slope of the absorption curve; (ml salt solution/g SAP sec)

As shown in FIG. 4C, the superabsorbent polymer particles absorbed saline solution at a higher rate in the initial 5 minutes, reached a swelling equilibrium in about 15 minutes. Because of this phenomenon, the analysis of the SAP swelling process can be focused on the investigation of initial swelling rate to study the linear relationship of swelling capacity versus time when the swelling is below 60%. The Voigt-based swelling kinetic model may analyze the results of the free swelling capacity (FSC) and absorption under load (AUL) at 0.3 psi of the superabsorbent polymer in 0.9 weight % saline solution (synthetic urine solution).

Figure 4D:
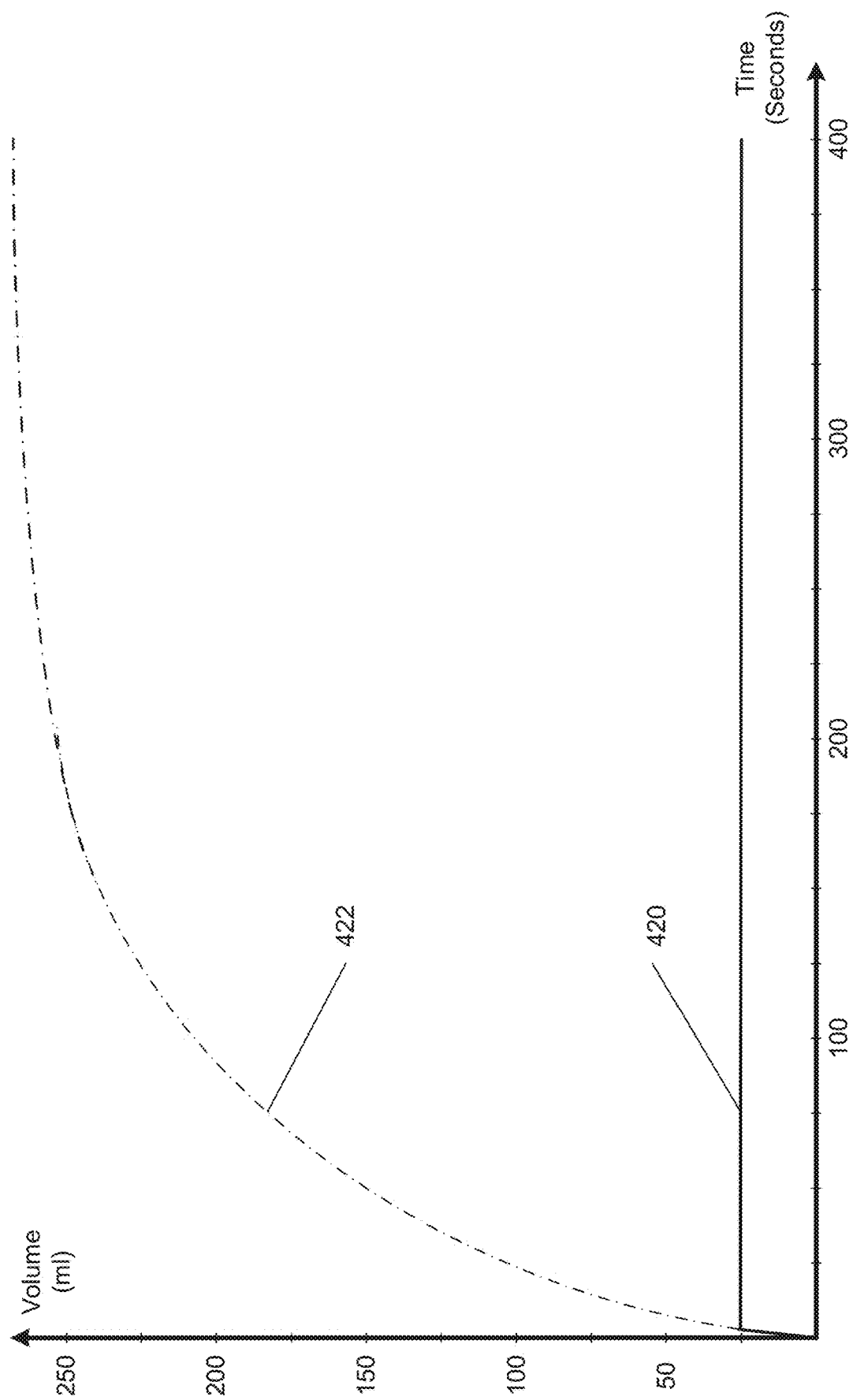
FIG. 4D illustrates a comparison of urine absorption performance of the disclosed reusable incontinence underwear to a conventional incontinence underwear according to aspects of the present disclosure.

FIG. 4D illustrates an exemplary graphical representation of urine absorption performance of the disclosed reusable incontinence underwear to a conventional incontinence underwear according to aspects of the present disclosure. As shown in FIG. 4D, the curve with solid line 420 represents urine absorption performance of the disclosed reusable incontinence underwear, and the curve with dashed line 422 represents urine absorption performance of a conventional incontinence underwear. With the disclosed reusable incontinence underwear, about 95% of the urine will be drained to the one or more urine collection bags. The remaining 5% of the urine will be initially absorbed by the urine transfer pouch, and subsequently absorbed by the one or more urine absorption pads in the middle layer of the reusable incontinence underwear. Even using a smaller amount of SAP powders, the disclosed reusable incontinence underwear can be able to absorb a typical urine out of the user within seconds, and thus keep the user dry. With the disclosed mechanism, the disclosed reusable incontinence underwear can be ready to handle the subsequent urine outputs from the user within seconds.

On the other hand, with a conventional incontinence underwear, it would need to absorb 100% of the user's urine output, which can take minutes to absorb the urine, even with a larger amount of SAP powders used due to the swelling effect discussed in association with FIG. 4C. In addition, once the conventional incontinence underwear is used once, its ability to absorb subsequent urine outputs from the user deteriorates significantly. This drawback renders the conventional incontinence underwear unsuitable for an extended period of time, such as more than half a day.

For example, the average urine output of a senior user is about 1.0 ml/kg/hr. Assuming the user weighs 65 kg and urinates once every 4 hours, the user may produce an urine output about 260 ml in the 4 hours duration (1.0 ml/kg/hr×65 kg×4 hrs=260 ml).

Case 1: Free swell capacity (FSC, also referred to as free absorption rate) of a commercial superabsorbent polymer sample in 0.9 weight % saline solution (used for the disclosed reusable incontinence underwear). The values of $A\infty$ and T can be determined using:

$A\infty(g/g)$ = approximately 47 g saline solution/g $SAP$ at $t$ = 1000 sec $A_t(g/g) = 0.632 \, A\infty$
    = 29.7 g saline solution/g $SAP$ at $t$ = 200 sec = $T$ $A_t$ vs absorption time : linear relation $dA_t/dt = 29.7/200 = 0.148$ g/g $SAP$ sec
    = 0.148 ml/g $SAP$ sec (slope)

Using the disclosed urine guide, 90% of 260 ml urine output will be drained away from the genital during urination, leaving about 26 ml of urine may remain in the urine guide to be absorbed by the urine absorbent pad. The urine absorbent pad of a 6×3 configuration may contains 7.2 grams of SAP particles, which means 1 gram of SAP is used to absorb 3.75 ml of urine.

time=3.75 ml/0.148 ml/1 g×sec=25 sec

Thus, it would take about 25 seconds to absorb the 26 ml of urine which is trapped in the urine transfer pouch for drying the genital area.

Case 2: Absorption under Load (AUL) by the conventional incontinence underwear at 0.3 psi using the same superabsorbent polymer sample in 0.9 weight % saline solution:

$A\infty(g/g) = 19.04$ g saline solution/g $SAP$ $A(g/g) = 0.632 \, A\infty = 12.1$ g saline solution/g $SAP$ at $t$ = 200 sec = $T$ $A_t$ vs sorption time : linear relation $dA_t/dt = 12.1/200 = 0.06$ ml urine/g $SAP$ /sec (slope)

In the case of a conventional incontinence underwear containing 21.5 grams of SAP particles, 1 gram of SAP would need to absorb 12.1 ml of urine.

time=12.1 ml/0.06 ml/1 g×sec=approximately 200 sec

Thus, the conventional incontinence underwear would need 200 seconds, to absorb the 260 ml of urine output for drying the genital area.

According to aspects of the present disclosure, the improved urine absorption mechanism of the disclosed reusable incontinence underwear can be achieved through the design of the support frame, the urine guide, the urine transfer pouch, and the urine absorbent pads. First, the support frame is made of a flexible polydimethylsiloxane which is resistant to body fluids and can be washed with 70% to 80% ethanol to sterilize the support frame. The support frame has a compressive strength range from 28.4 to 51.7 GPa, enabling it to support the urine transfer pouch and urine absorbent pads without experiencing external pressure. As a result, it functions to prevent rewet and rash.

The urine guide is designed to drain about 90% to 95% urine output away from the genital to the urine transfer pouch and the urine absorbent pad during urination. This enables the disclosed reusable incontinence underwear to absorb a typical amount of urine output in significantly less time than a conventional incontinence underwear as discussed above.

The urine transfer pouch is designed to hold the urine output during urination and then wick the urine away from the urine transfer pouch to the urine absorbent pads, giving SAP particles in the urine absorbent pads time to absorb a user's urine output held by the urine transfer pouch. After the urine transfer pouch is dried by the urine absorbent pads, it is ready to catch the subsequent cycles of urination. By selecting a moisture wicking fabric to make the urine transfer pouch, urine can be drawn away from the genital area of the user.

According to aspects of the present disclosure, microfiber used in the urine transfer pouch can provide desired absorbency due to greater surface area available to absorb urine and moisture. For example, a 70% polyester/30% polyamide blend 300 GSM microfiber that is capable of absorbing 7 or more times of its weight in liquid can be used. In addition, the initial absorption speed of a microfiber fabric can be shown that the absorption speed of a 5 inches by 5 inches microfiber sample can be completely saturated with water in less than five seconds. For these reasons, the disclosed incontinence underwear uses microfiber to make the urine transfer pouch.

In an exemplary implementation, the urine transfer pouch can be made using a micro fiber such as a 2 to 3 mm thick 70% polyester/30% polyamide 300 GSM microfiber pad. The total surface area of the urine transfer pouch can be around 352 square em, which includes the surface area of the front double layer microfiber pad is about of 168 square cm (14 cm×6 cm×2 layer); the surface area of the middle microfiber pad in the urine guide is about of 16 square cm (11 cm×3 mm×0.5=16.5); and the surface area of the rear double layer microfiber pad is about of 168 square cm (14 cm×6 cm×2 layer), The weight of the urine transfer pouch can be about 10.56 grams (352 square cm×300 g/square m=10.56 gram). Water absorption capacity of microfiber is approximately 7 ml/g in 4 seconds, which means that the urine transfer pouch has the capacity to absorb 70.92 ml of urine in about 4 seconds (10.56 gram×7 ml/g=70.92 ml). Therefore, the urine transfer pouch can hold all of the 36 ml of a typical user's urine output, which in turn enables the urine transfer pouch to have the capability to keep the genital area of the user dry a few seconds after urination.

The urine absorbent pad is formed with a group of uniformly distributed collection cups, where each cup may contain 200 to 400 milligram of superabsorbent polymer (SAP) particles. The collection cups provide room for expansion when superabsorbent polymer particles get in contact with urine to undergo free swelling. As shown in FIG. 4C, for free swelling capacity 1 gram of SAP particles may absorb 47 ml of urine. In one implementation, one piece of 6×1 configuration urine absorbent pad 14 cm×2.5 cm×1 cm containing 1.2 to 2.4 grams of SAP particles may have a urine absorption capacity of 56 to 112 ml. This capability can extend the period of changing the disclosed reusable incontinence underwear to 8 hours, such as overnight, for example.

However, in conventional incontinence underwear, the stiff fiber matrix can create a compressive force, for example as much as 0.3 psi on the superabsorbent polymer particles. This compressive force causes the superabsorbent polymer particles to undergo an absorption under load (AUL) swelling process, which in turn reduces urine absorption capacity of the conventional incontinence underwear.

On the other hand, in some implementations of the reusable incontinence underwear, 90% to 95% of the urine output may be drained by the urine guide during urination to the urine collection bags. That is, about 13 ml to 26 ml urine (90% to 95% of 260 ml in 4 hours during) may be drained by the urine guide to the rear double layer microfiber pad made of 300 GMS microfiber which has a surface area of about 168 square cm (14 cm×6 cm×2 layers=168; dimension of the rear double layer microfiber pad 14 cm×6 cm×4 mm) and it weighs about 5 grams (168 square cm×300 g/square m=5 gram). The water absorption capacity of the rear double layer microfiber is about 7 ml/g in 4 seconds. This means that the rear double layer microfiber pad has the capacity to bold 35 ml of urine in 4 seconds (the water absorption capacity of microfiber 7 ml/g in 4 seconds; 5 gram×7 ml/g microfiber=35 ml) so it has absorbent capacity to hold this 13 to 26 ml of urine output.

The middle vertical striped microfiber pad possesses wicking properties to transfer the remaining urine from the rear microfiber pad to the front microfiber pad, or vice versa. Together, the rear and the front microfiber pads share the load of holding 13 to 26 ml of the remaining urine. Both the rear and the front microfiber pads can be dried out by the urine absorbent pads within minutes, therefore the urine transfer pouch may be used repeatedly to absorb urine output next time when the user urinates.

The urine transfer pouch possesses wicking properties to transfer collected urine from the rear double layer microfiber pad to the front double layer microfiber pad, or vice versa. Together, the rear and the front double layer pads share the load of holding 13 to 26 ml of urine. Both the rear and the front double layer pads can be dried out by the urine absorbent pads within minutes, therefore the urine transfer pouch may be used repeatedly to absorb urine output next time when the user urinates.

Figure 5A:
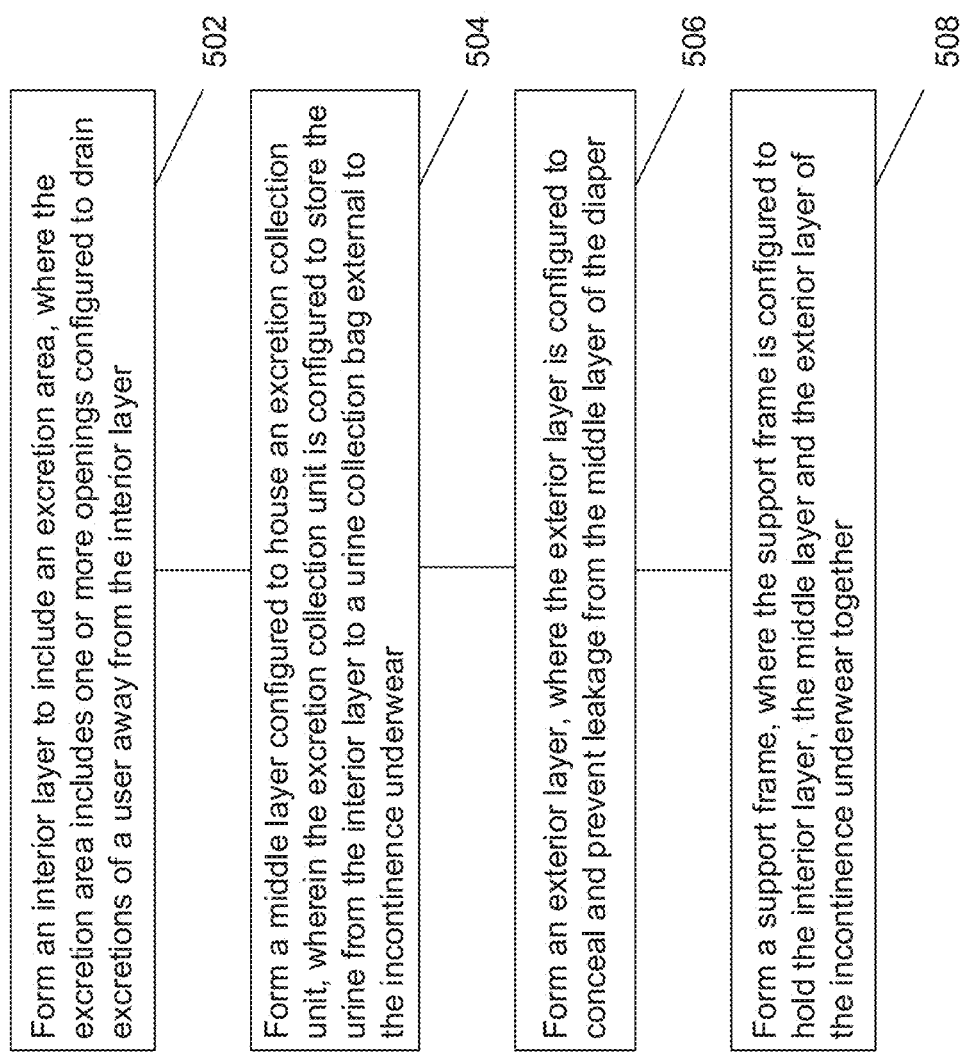
FIG. 5A illustrates an exemplary method of manufacturing an incontinence underwear according to aspects of the present disclosure.

FIG. 5A illustrates an exemplary method of manufacturing a reusable incontinence underwear according to aspects of the present disclosure. As shown in FIG. 5A, in block 502, the method forms an interior layer to include an excretion area, where the excretion area includes one or more openings configured to drain excretions of a user away from the interior layer. The interior layer is formed using a hydrophobic material configured to repel the excretions of the user to the middle layer of the incontinence underwear. In block 504, the method forms a middle layer configured to house an excretion collection unit, where the excretion collection unit is configured to store the urine from the interior layer to a urine collection bag external to the incontinence underwear. In block 506, the method forms an exterior layer, where the exterior layer is configured to conceal and prevent leakage from the middle layer of the incontinence underwear. The exterior layer is formed using a breathable material to allow moisture from the middle layer to escape the incontinence underwear. In block 508, the method forms a support frame, where the support frame is configured to hold the interior layer, the middle layer and the exterior layer of the incontinence underwear together.

Figure 5B:
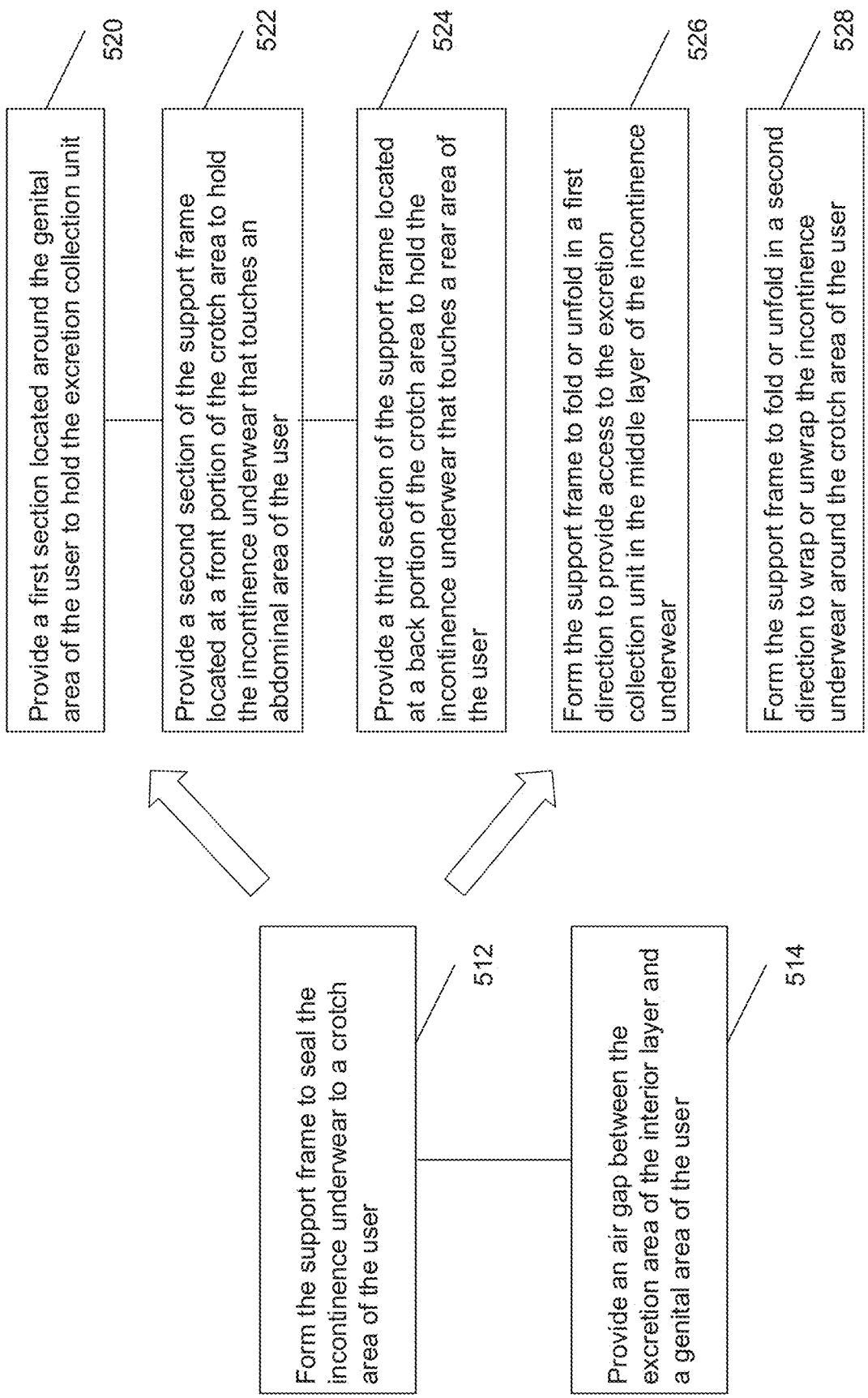
FIG. 5B illustrates an exemplary method of forming a support frame of the reusable incontinence underwear of FIG. 5A according to aspects of the present disclosure.

FIG. 5B illustrates an exemplary method of forming a support frame of the reusable incontinence underwear of FIG. 5A according to aspects of the present disclosure. In the example shown in FIG. 5B, in block 512, the method forms the support frame to seal the incontinence underwear to a crotch area of the user. In block 514, the method provides an air gap between the excretion area of the interior layer and a genital area of the user.

According to aspects of the present disclosure, the methods performed in block 512 may further include the methods performed in blocks 520, 522, and 524. In block 520, the method provides a first section located around the genital area of the user to hold the excretion collection unit. In block 522, the method provides a second section of the support frame located at a front portion of the crotch area to hold the incontinence underwear that touches an abdominal area of the user. In block 524, the method provides a third section of the support frame located at a back portion of the crotch area to hold the incontinence underwear that touches a rear area of the user. The support frame is made of polydimethylsiloxane rubber or thermoplastic elastomers, and is configured to wrap around the crotch area of the user to prevent leakage.

Moreover, the methods performed in block 512 may further include the methods performed in blocks 526 and 528. In block 526, the method forms the support frame to fold or unfold in a first direction to provide access to the excretion collection unit in the middle layer of the incontinence underwear. In block 528, the method forms the support frame to fold or unfold in a second direction to wrap or unwrap the incontinence underwear around the crotch area of the user.

Figure 5C:
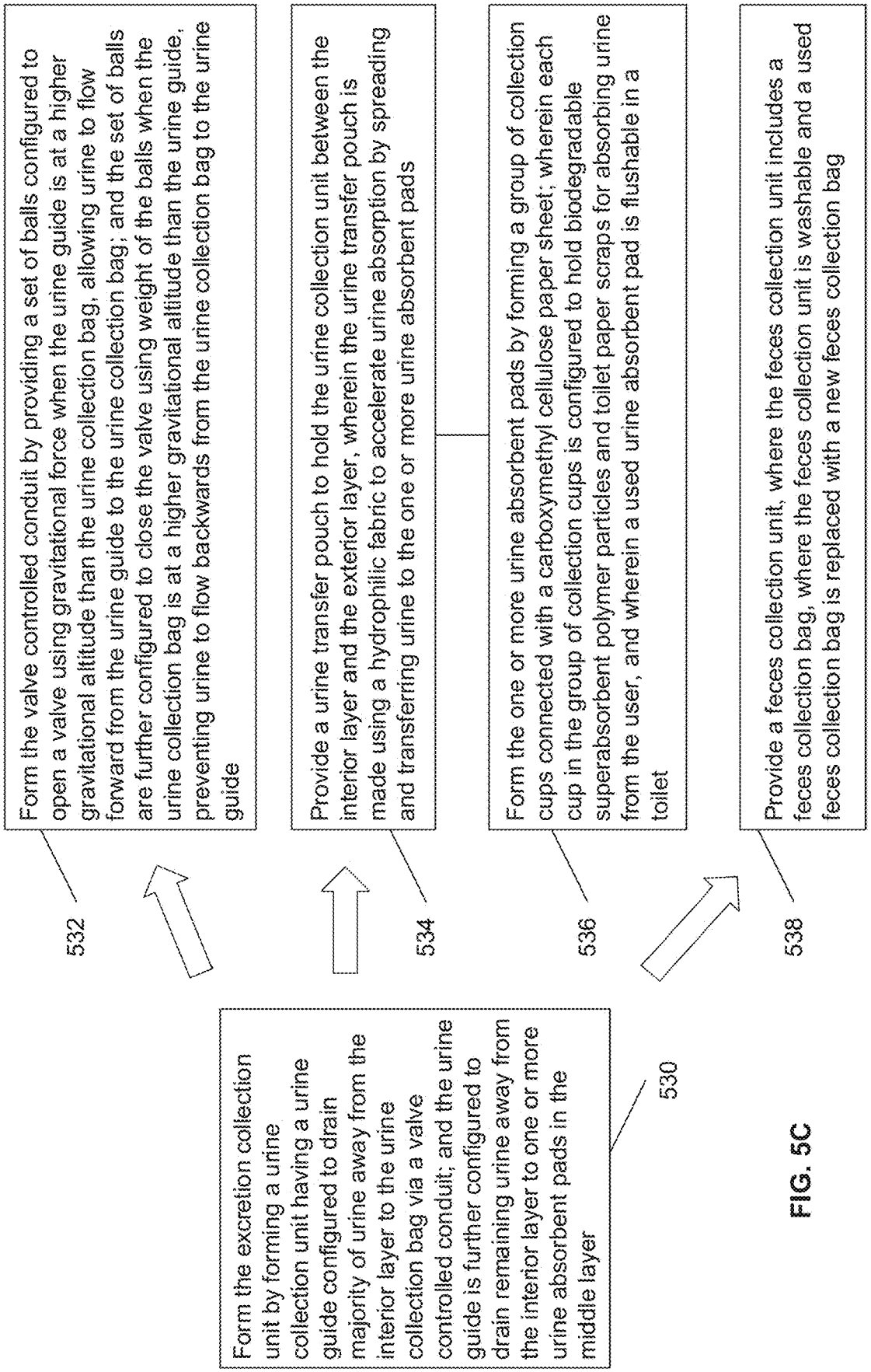
FIG. 5C illustrates an exemplary method of forming an excretion collection unit of the reusable incontinence underwear of FIG. 5A according to aspects of the present disclosure.

FIG. 5C illustrates an exemplary method of forming an excretion collection unit of the reusable incontinence underwear of FIG. 5A according to aspects of the present disclosure. In the exemplary method shown in FIG. 5C, in block 530, the method forms the excretion collection unit by forming a urine collection unit having a urine guide configured to drain majority of urine away from the interior layer to the urine collection bag via a valve controlled conduit. The urine guide is further configured to drain remaining urine away from the interior layer to one or more urine absorbent pads in the middle layer. The urine collection bag is made of polydimethylsiloxane rubber; and where the urine collection bag is detachable from the incontinence underwear for disposal of collected urine and for cleaning.

According to aspects of the present disclosure, the methods performed in block 530 may further include the methods performed in blocks 532, 534, 536, and/or 538. In block 532, the method forms the valve controlled conduit by providing a set of balls configured to open the valve using gravitational force when the urine guide is at a higher gravitational altitude than the urine collection bag, allowing urine to flow forward from the urine guide to the urine collection bag. The set of balls are further configured to close the valve using weight of the balls when the urine collection bag is at a higher gravitational altitude than the urine guide, preventing urine to flow backwards from the urine collection bag to the urine guide.

In block 534, the method provides a urine transfer pouch to hold the urine collection unit between the interior layer and the exterior layer, where the urine transfer pouch is made using a hydrophilic fabric to accelerate urine absorption by spreading and transferring urine to the one or more urine absorbent pads.

In block 536, the method forms the one or more urine absorbent pads by forming a group of collection cups connected with a carboxymethyl cellulose paper sheet; where each cup in the group of collection cups is configured to hold biodegradable superabsorbent polymer particles and toilet paper scraps for absorbing urine from the user, and where a used urine absorbent pad is flushable in a toilet.

In block 538, the method provides a feces collection unit, where the feces collection unit includes a feces collection bag, where the feces collection unit is washable and a used feces collection bag is replaced with a new feces collection bag.

FIG. 6A illustrates a top view of an exemplary implementation of a feces sensing unit according to aspects of the present disclosure. As shown in FIG. 6A, the feces sensing unit 600 is made of a hydrophobic film, which includes two sensing openings located between three moisture barriers 602, 604, and 606. The feces sensing unit may be adhered on the bottom surface of the feces collection bag. The moisture barriers are used to form a cathodic sensing element 610 and an anodic sensing element 612. The width of the moisture barrier 604 is about 1 centimeter, which is used to isolate the cathodic sensing element 610 from the anodic sensing element 612 electrically and ionically. The feces sensing unit 600 can be located at the bottom inside surface of a feces collection bag.

According to aspects of the present disclosure, The cathodic sensing element 610 and the anodic sensing element 612 are made of ionic conducting gel which are coated on a flushable rayon nonwoven fabric film. The cathodic sensing element 610 may be adhered in the area between moisture barrier 602 and 604; and the anodic sensing element 612 may be adhered in the area between moisture barrier 604 and 606. The ionic conducting gel may be prepared by heating a mixture of 3% agar in 1 M KCl solution. The hot agar solution is used to form the cathodic sensing element 610 and the anodic sensing element 612, by coating the hot agar solution on the flushable rayon nonwoven fabric film. Capillary action draws the hot agar solution into the pores of the flushable rayon nonwoven fabric film. When the agar solution is cooled and the pores of the rayon nonwoven fabric film are filled with ionic conducting gel configured to form the cathodic sensing element 610 and the anodic sensing element 612 in gelled forms respectively.

Note that in the clean condition as shown in FIG. 6A, the moisture barrier 604 forms a gap between the cathodic sensing element 610 and the anodic sensing element 612, so that the cathodic sensing element 610 is ionically isolated from the anodic sensing element 612.

FIG. 6B illustrates the feces sensing unit of FIG. 6A with feces according to aspects of the present disclosure. Note that some elements shown in FIG. 6B are similar to the corresponding elements shown in FIG. 6A. The descriptions of such elements are not repeated for simplicity. In the example of FIG. 6B, when the discharged feces 608 drop on the bottom surface of the feces collection bag, the feces may directly cover the cathodic sensing element 610, the anodic sensing element 612 and the moisture barrier line 604. The discharged feces contains water moisture and salt which can serve as an activated salt bridge. The activated salt bridge that forms an ionic link that closes the conductive circuit between the cathodic sensing element 610 and the anodic sensing element 612.

Figure 6C:
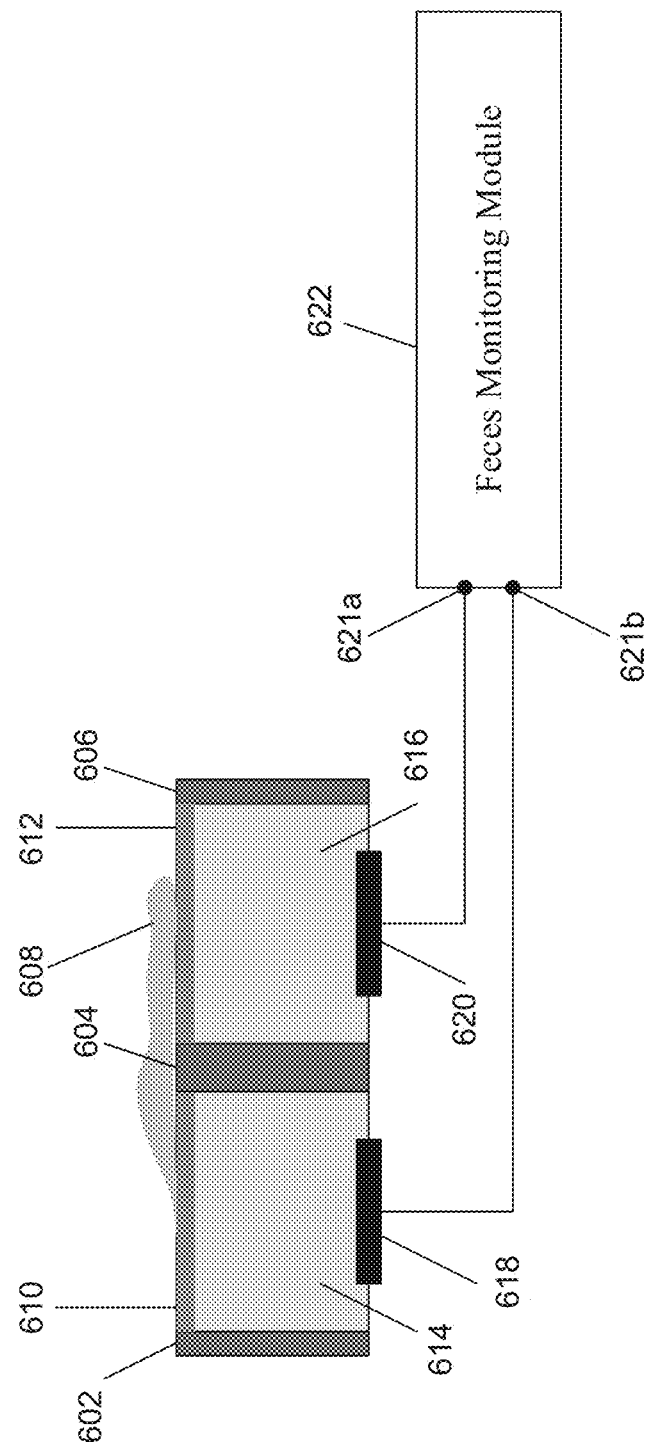
FIG. 6C illustrates a side view of the exemplary feces sensing unit of FIG. 6B with connection to a feces monitoring module according to aspects of the present disclosure.

FIG. 6C illustrates a side view of the exemplary feces sensing unit of FIG. 6B with connection to a feces monitoring module according to aspects of the present disclosure. In the example shown in FIG. 6C, a cathode terminal includes a cathodic sensing element 610, a cathodic salt bridge cap 614 and a cathode electrode 618. An anode terminal includes an anodic sensing element 612, an anodic salt bridge cap 616 and an anode electrode 620. In an inactive state, the cathode terminal is ionically isolated from the anode terminal by the moisture barrier 604.

In some implementations, the cathodic salt bridge cap 614 and the anodic salt bridge cap 616 are made of eco-friendly sponge such as hemp or bamboo sponge. Then, the cathodic salt bridge cap 614 may be prepared by dipping and pressing a flexible hemp or bamboo sponge into a cathodic electrolyte such as a 1 M NaNO3 solution that contains about 0.01 to 0.1 M AgNO3 and a hygroscopic salt such as 0.1 M MgCl2. Capillary action can draw the cathodic electrolyte into the pores of the hemp or bamboo sponge. Then, the cathodic salt bridge cap 614 obtains ionic conductivity capabilities.

The anodic salt bridge cap 616 may be prepared by dipping and pressing a flexible hemp or bamboo sponge into an anodic electrolyte such as a 1 M NaNO3 solution and a hygroscopic salt such as 0.1 M MgCl2. Capillary action can draw the anodic electrolyte into the pores of the hemp or bamboo sponge. Then, the anodic salt bridge cap 616 obtains ionic conductivity capabilities.

The upper surface of the cathodic salt bridge cap 614 is in contact with the cathodic sensing element 610 and the lower surface of the cathodic salt bridge cap 614 is in contact with the cathode electrode 618 such as a silver electrode.

The upper surface of the anodic salt bridge cap 616 is in contact with the anodic sensing element 612 and the lower surface of the cathodic salt bridge cap 616 is in contact with the anode electrode 620 such as a zine electrode.

According to aspects of the present disclosure, when a user's discharged feces covered the cathodic sensing element 610, the anodic sensing element 612 and the moisture barrier line 604, the discharged feces may serve as an activated salt bridge that forms an ionic link that closes the conductive circuit between the cathodic sensing element 610 and the anodic sensing element 612. Note that the self-activated galvanic cell such as a zinc-silver galvanic cell can be used to power other electronic components, such as to power a passive RFID tag.

The conductive circuit loop starts from the cathode electrode 618, then continue through the cathodic salt bridge cap 614, the activated salt bridge 608, the anodic salt bridge cap 616, the anode electrode 620, a first terminal 621a of a feces monitoring module 622, a second terminal 621b of the feces monitoring module 622, and back to the cathode electrode 618.

In some embodiments, the self-activated galvanic cell such as a zinc-silver galvanic cell may serve as a power source to power a passive RFID tag. For example a Zn—Ag self-activated galvanic cell may provide 1.5 V dc power to operate a galvanic cell powered RFID tag, which can be used to identify a user, and the identification of the user may be transmitted to a caregiver.

Figure 7:
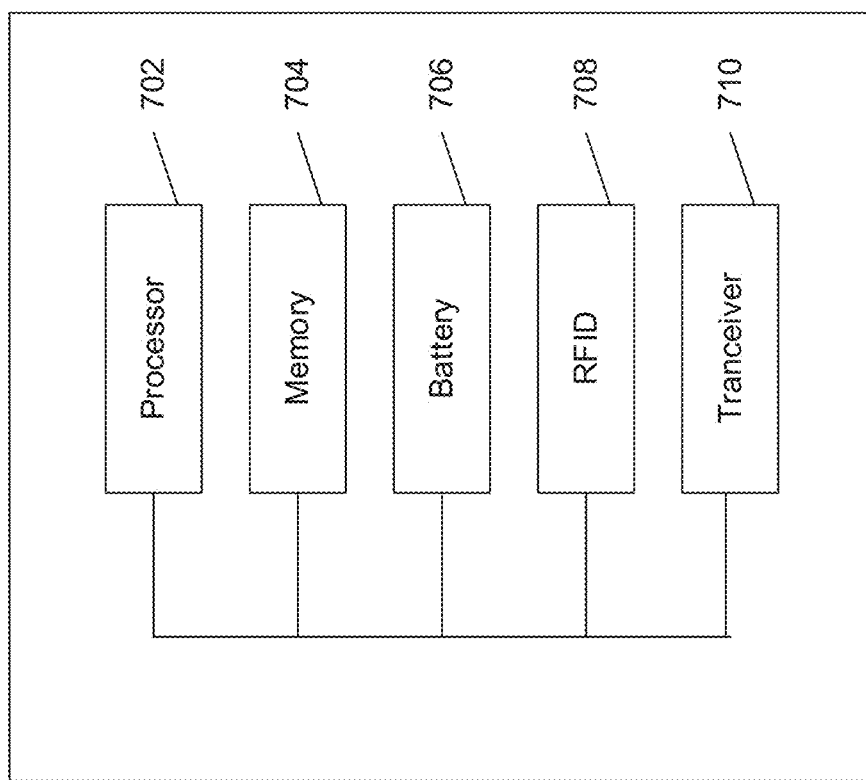
FIG. 7 illustrates an exemplary implementation of a feces monitoring module according to aspects of the present disclosure.

FIG. 7 illustrates an exemplary implementation of a feces monitoring module according to aspects of the present disclosure. In the exemplary implementation of FIG. 7, the feces monitoring module may include process 702, memory 704, battery 706, RFID 708, and transceiver 710. The memory 704 may be configured to store information about operational parameters of the reusable incontinence underwear, including information about one or more caregivers and their corresponding one or more cellular phones. The battery 706 may be a lithium battery up to 1.5V. In some embodiments, the battery 706 may be optional, as power may be supplied by the galvanic cell described in association with FIG. 6C. The RFID 708 may be a passive RFID or an active RFID. In the case of a passive RFID is used, its power may be supplied by the galvanic cell described in association with FIG. 6C. In the case of an active RFID, its power may be supplied by the battery 706. The transceiver 710, controlled by process 702, is configured to communicate status of the user with one or more caregivers. For example, the status of the user may include the RFID assigned to the user via the reusable incontinence underwear being worn by the user. The status of the user may further include a feces sensed signal that indicates whether feces is sensed in the reusable incontinence underwear worn by the user. The transceiver 710 may use any commercial wireless protocols, such as Bluetooth or near field communication (NFC), in its communication with the one or more caregivers.

Figure 8A:
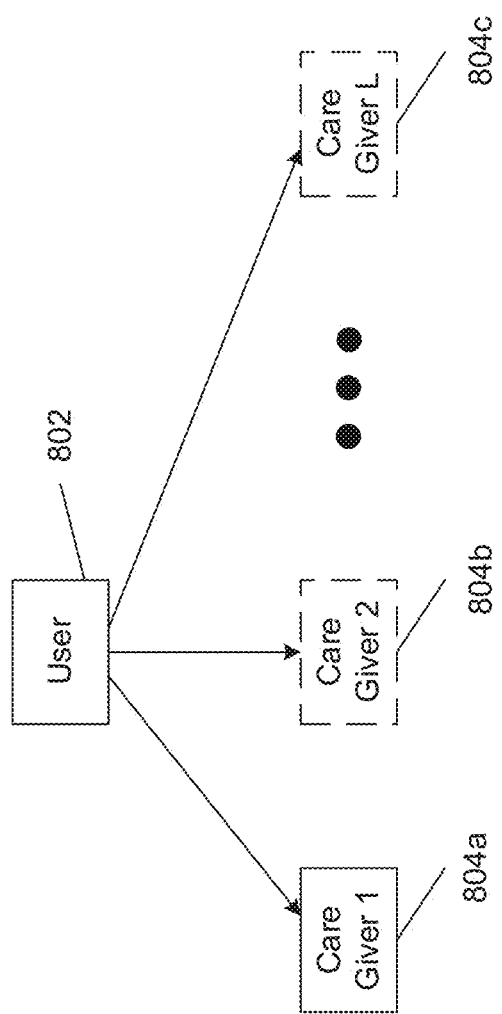
FIG. 8A illustrates an exemplary use of a reusable incontinence underwear with feces sensing in an environment of a single user according to aspects of the present disclosure.

FIG. 8A illustrates an exemplary use of a reusable incontinence underwear with feces sensing in an environment of a single user according to aspects of the present disclosure. As shown in FIG. 8A, user 802 may be paired with one or more caregivers, such as caregiver 1 (804a), caregiver 2 (804b), and/or caregiver L (804c). This case is likely to be implemented in a home-care environment. In the event of multiple caregivers, one caregiver, for example caregiver 1, may be assigned as the primary caregiver. Notification signals can be sent to the primary caregiver first. In the event there is no response by the primary caregiver within a predetermined period of time such as a few minutes, other caregivers in the group will be notified. In some implementations, a round-robin scheme may be employed to establish the order of attending to the user, starting with the primary caregiver. In other implementations, a first-come-first-serve (FCFS) scheme may be employed to establish the order of attending to the user. With the FCFS scheme, the caregiver who has responded first will take care of the user.

Figure 8B:
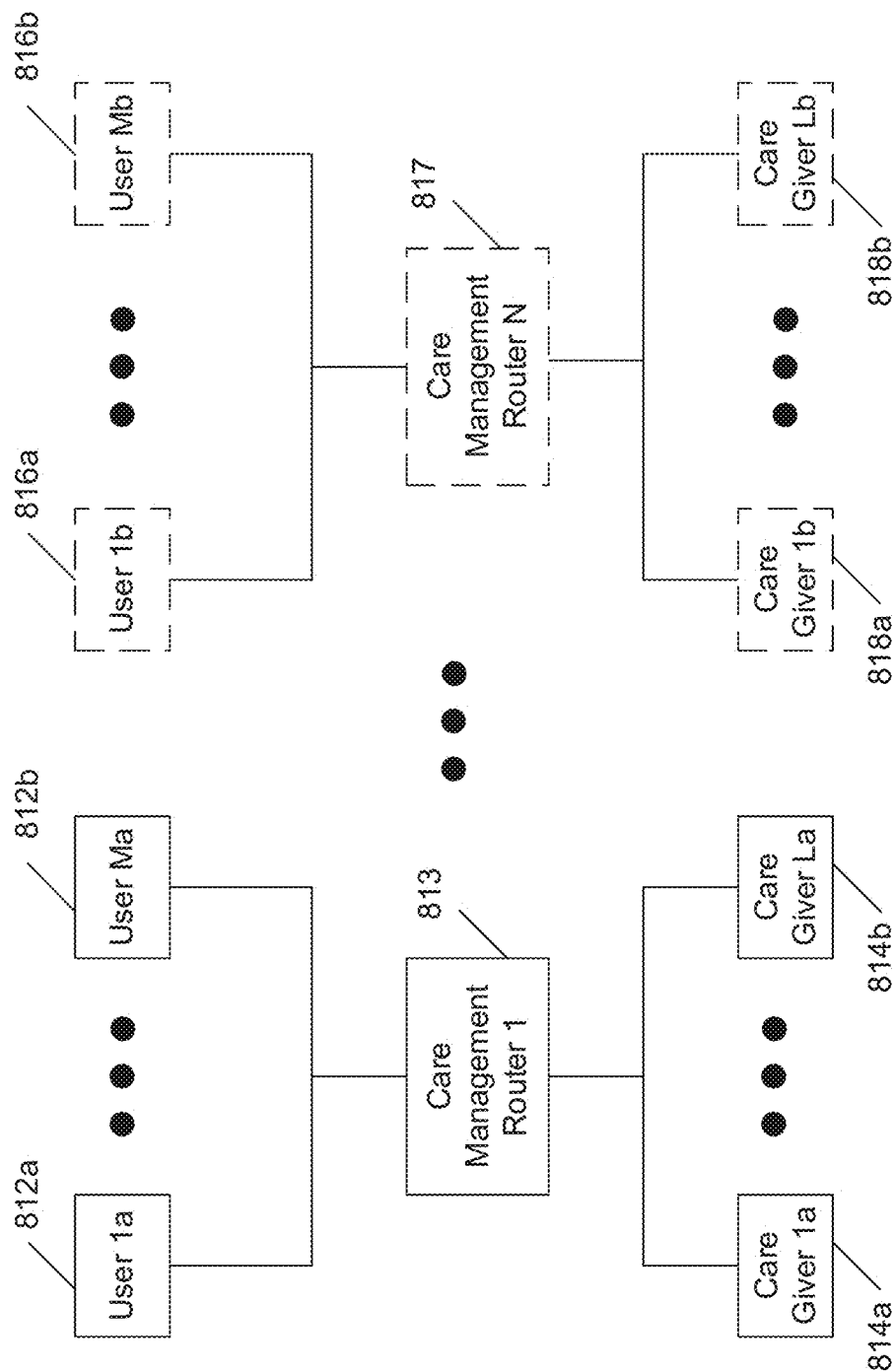
FIG. 8B illustrates an exemplary use of reusable incontinence underwear with feces sensing in an environment of multiple users according to aspects of the present disclosure.

FIG. 8B illustrates an exemplary use of reusable incontinence underwear with feces sensing in an environment of multiple users according to aspects of the present disclosure. As shown in the exemplary use of FIG. 8B, one or more groups of users can be cared for by corresponding one or more groups of caregivers. This case is likely to be implemented in a nursing home or infant care center environment. For example, a first group of users, such as user 1a (812a) through user Ma (812b), may be cared by caregiver 1a (814a) through caregiver La (814b), where the communication between user 1a (812a) through user Ma (812b) and caregiver 1a (814a) through caregiver La (814b) may be handled via care management router 1 (813).

According to aspects of the present disclosure, a care management router, such as the care management router 1 (813), may be configured to manage both the list of users to be cared for and the list of caregivers. Information of the users, such as each user's RFID, name, age, gender, location, and health information, may be stored in the care management router. In addition, information of the caregivers, such as each caregiver's smart phone number, user assignments, work shifts, and other relevant information are also stored in the care management router. As a result, when the care management router receives a feces sensed signal from any of the user, it can automatically identify a corresponding caregiver based on the information stored within the care management router, and send the caregiver a notification to take care of the user from whom the feces sensed signal is received.

In some embodiments, based on the service required by the users, each user may be assigned a primary caregiver, and the other caregiver may play a supplementary role to the primary caregiver. In other embodiments, a round-robin scheme or a FCFS scheme may be employed to establish the order of attending to the user, as described above in association with FIG. 8A.

Similarly, a second group of users, such as user 1b (816a) through user Mb (816b), may be cared by caregiver 1b (818a) through caregiver Lb (818b), where the communication between user 1b (816a) through user Mb (816b) and caregiver 1b (818a) through caregiver Lb (818b) may be handled via care management router 2 (817). Note that because different groups of users are being served, the operations of the first group and the second group may be independent of each other. For example, care management router 1 (813) may implement a scheme where each user is assigned a corresponding caregiver while care management router 2 (817) may implement a FCFS scheme of providing care services.

Figure 9A:
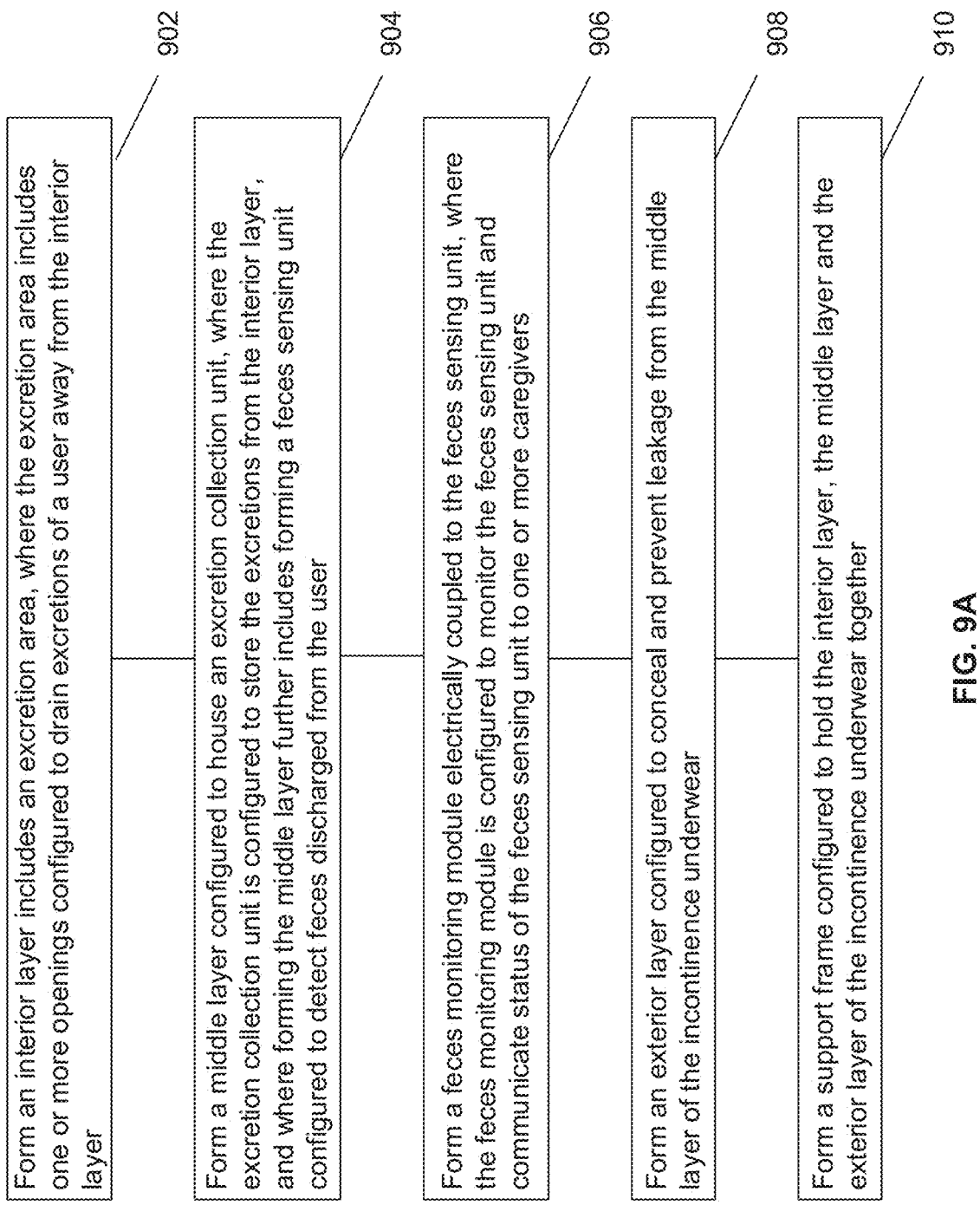
FIG. 9A illustrates an exemplary method of manufacturing a reusable incontinence underwear with feces sensing according to aspects of the present disclosure.

FIG. 9A illustrates an exemplary method of manufacturing a reusable incontinence underwear with feces sensing according to aspects of the present disclosure. As shown in FIG. 9A, in block 902, the method forms an interior layer that includes an excretion area, where the excretion area includes one or more openings configured to drain excretions of a user away from the interior layer. In block 904, the method forms a middle layer configured to house an excretion collection unit, where the excretion collection unit is configured to store the excretions from the interior layer, and where forming the middle layer further includes forming a feces sensing unit configured to detect feces discharged from the user. Note that the excretion collection unit includes a feces collection unit, where the feces collection unit includes a feces collection bag, and where the feces collection unit is washable and a used feces collection bag is replaced with a new feces collection bag. In block 906, the method forms a feces monitoring module electrically coupled to the feces sensing unit, where the feces monitoring module is configured to monitor the feces sensing unit and communicate status of the feces sensing unit to one or more caregivers. In block 908, the method forms an exterior layer configured to conceal and prevent leakage from the middle layer of the incontinence underwear. In block 910, the method forms a support frame configured to hold the interior layer, the middle layer and the exterior layer of the incontinence underwear together.

Figures 9B, 9C:
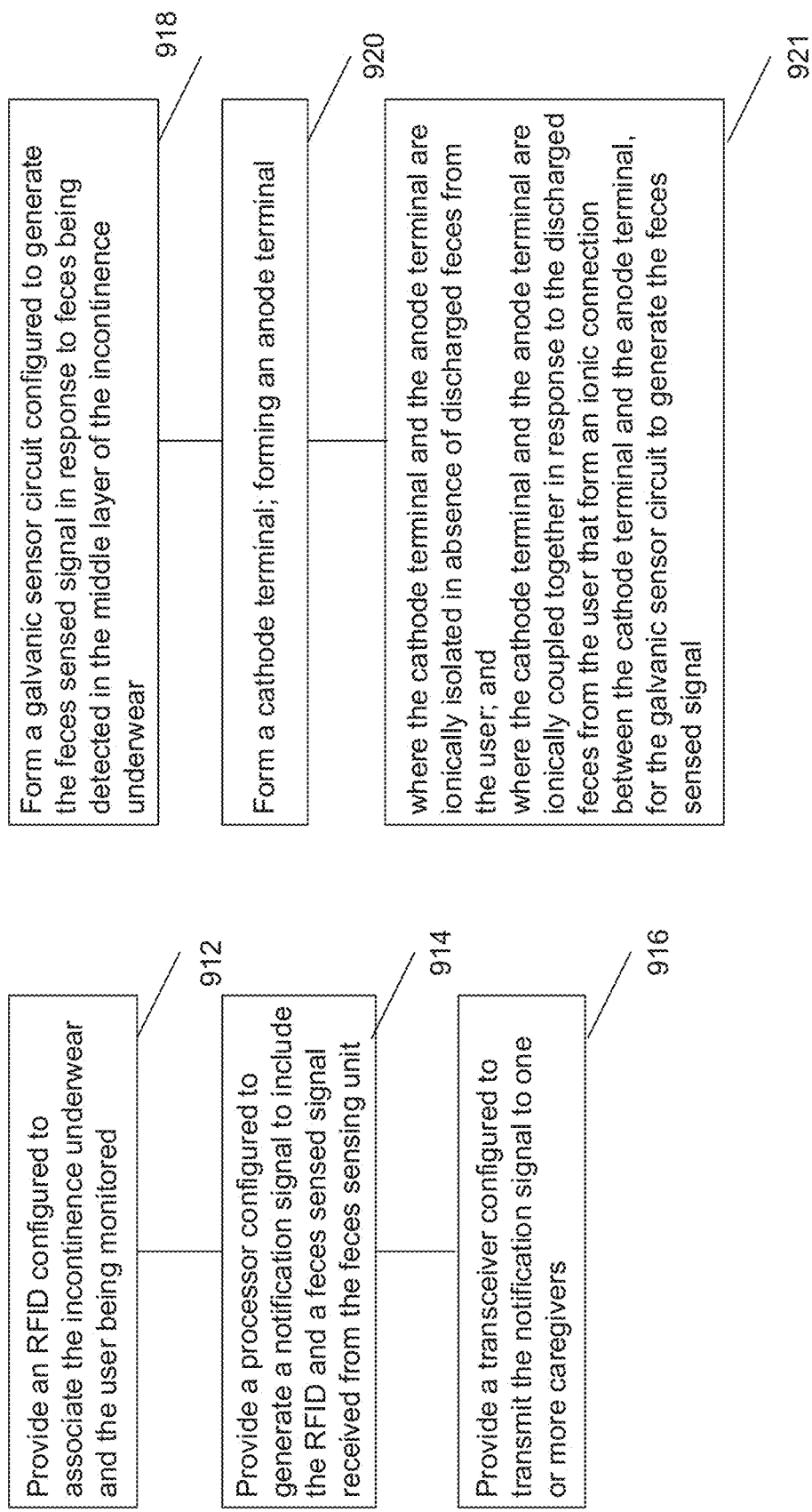
FIG. 9B illustrates an exemplary method of forming feces monitoring module according to aspects of the present disclosure.
FIG. 9C illustrates an exemplary method of forming a feces sensing unit according to aspects of the present disclosure.

FIG. 9B illustrates an exemplary method of forming feces monitoring module according to aspects of the present disclosure. In the exemplary method of FIG. 9B, in block 912, the method provides an RFID configured to associate the incontinence underwear and the user being monitored. In block 914, the method provides a processor configured to generate a notification signal to include the RFID and a feces sensed signal received from the feces sensing unit. In block 916, the method provides a transceiver configured to transmit the notification signal to one or more caregivers.

Note that the method of providing the RFID includes providing a passive RFID, where the passive RFID is powered by a current generated by the galvanic sensor circuit in response to the discharged feces from the user that forms an ionic connection between the cathode terminal and the anode terminal of the galvanic sensor circuit. The method of providing the transceiver includes performing two way communications with one or more preapproved cellular phones or one or more preapproved care management devices via a wireless communication protocol.

FIG. 9C illustrates an exemplary method of forming a feces sensing unit according to aspects of the present disclosure. As shown in the exemplary method of FIG. 9C, in block 918, the method forms a galvanic sensor circuit configured to generate the feces sensed signal in response to feces being detected in the middle layer of the incontinence underwear.

The method of block 918 may further include the methods performed in block 920 and block 921. In block 920, the method forms a cathode terminal, and forms an anode terminal. In block 921, the cathode terminal and the anode terminal are ionically isolated in absence of discharged feces from the user; and the cathode terminal and the anode terminal are ionically coupled together in response to the discharged feces from the user that form an ionic connection between the cathode terminal and the anode terminal, for the galvanic sensor circuit to generate the feces sensed signal.

According to aspects of the present disclosure, the cathode terminal includes a cathodic sensing element, a cathodic salt bridge, and a cathode electrode, where the cathodic sensing element, the cathodic salt bridge, and the cathode electrode are ionically coupled together. The anode terminal includes an anodic sensing element, an anodic salt bridge, and an anode electrode, where the anodic sensing element, the anodic salt bridge, and the anode electrode are ionically coupled together. The ionic connection is formed between the cathodic sensing element and the anodic sensing element by the discharged feces from the user.

FIG. 9D illustrates an exemplary method of pairing a feces monitoring module according to aspects of the present disclosure. As shown in FIG. 9D, in block 922, the method pairs the feces monitoring module with one or more preapproved cellular phones in situations where an individual user is being monitored.

The method performed in block 922 may further include the methods performed in block 924, block 926 or block 928. In block 924, the method directs the notification signal to a preapproved cellular phone of a caregiver. In block 926, the method directs the notification signal to a group of preapproved cellular phones of caregivers in a round-robin manner and in an order of a predetermined priority. In block 928, the method broadcasts the notification signal to the group of preapprove cellular phones of caregivers.

FIG. 9E illustrates another exemplary method of pairing a feces monitoring module according to aspects of the present disclosure. In the example of FIG. 9E, in block 932, the method pairs the feces monitoring module with one or more preapproved care management devices in situations where a group of users are being monitored. In block 934, the one or more preapproved care management devices are configured to redirect the notification signal to one or more caregivers on duty according to duty assignment of caregivers, date, and time of a work shift.

One skilled in the relevant art will recognize that many possible modifications and combinations of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the invention to the precise forms disclosed. Many modifications and variations are possible in view of the above teachings. The embodiments were chosen and described to explain the invention and their practical applications, and to enable others skilled in the art to best utilize the invention and various embodiments with various modifications as suited to the particular use contemplated.

What is claimed is:

1. An incontinence underwear, comprising:
   an interior layer includes an excretion area, wherein the excretion area includes one or more openings configured to drain excretions of a user away from the interior layer;
   a middle layer configured to house an excretion collection unit, wherein the excretion collection unit is configured to store the excretions from the interior layer, and wherein the middle layer further includes a feces sensing unit configured to detect feces discharged from the user, wherein the feces sensing unit comprises a moisture barrier having openings covered with a conductive gel;
   a feces monitoring module electrically coupled to the feces sensing unit, wherein the feces monitoring module is configured to monitor the feces sensing unit and communicate status of the feces sensing unit to one or more caregivers;
   an exterior layer configured to conceal and prevent leakage from the middle layer of the incontinence underwear; and
   a support frame configured to hold the interior layer, the middle layer and the exterior layer of the incontinence underwear together.

2. The incontinence underwear of claim 1, wherein the feces monitoring module comprises:
   an RFID configured to associate the incontinence underwear and the user being monitored;
   a processor configured to generate a notification signal to include the RFID and a feces sensed signal received from the feces sensing unit; and
   a transceiver configured to transmit the notification signal to one or more caregivers.

3. The incontinence underwear of claim 2, wherein the feces sensing unit comprises:
   a galvanic sensor circuit configured to generate the feces sensed signal in response to feces being detected in the middle layer of the incontinence underwear.

4. The incontinence underwear of claim 3, wherein the galvanic sensor circuit comprises:
   a cathode terminal;
   an anode terminal;
   wherein the cathode terminal and the anode terminal are ionically isolated by the moisture barrier in absence of discharged feces from the user; and
   wherein the cathode terminal and the anode terminal are ionically coupled together in response to the discharged feces from the user that form an ionic connection between the cathode terminal and the anode terminal for the galvanic sensor circuit to generate the feces sensed signal.

5. The incontinence underwear of claim 4, wherein
   the cathode terminal comprises a cathodic sensing element, a cathodic salt bridge, and a cathode electrode, wherein the cathodic sensing element, the cathodic salt bridge, and the cathode electrode are ionically coupled together;
   the anode terminal comprises an anodic sensing element, an anodic salt bridge, and an anode electrode, wherein the anodic sensing element, the anodic salt bridge, and the anode electrode are ionically coupled together; and
   wherein the ionic connection is formed between the cathodic sensing element and the anodic sensing element by the discharged feces from the user.

6. The incontinence underwear of claim 2, wherein the RFID comprises:
   a passive RFID, wherein the passive RFID is powered by a current generated by the galvanic sensor circuit in response to the discharged feces from the user that forms an ionic connection between the cathode terminal and the anode terminal of the galvanic sensor circuit.

7. The incontinence underwear of claim 2, wherein the processor is further configured to:
   pair the feces monitoring module with one or more preapproved cellular phones in situations where an individual user is being monitored;
   direct the notification signal to a preapproved cellular phone of a caregiver; or
   direct the notification signal to a group of preapproved cellular phones of caregivers in a round-robin manner and in an order of a predetermined priority; or
   broadcast the notification signal to the group of preapprove cellular phones of caregivers.

8. The incontinence underwear of claim 2, wherein the processor is further configured to:
   pair the feces monitoring module with one or more preapproved care management devices in situations where a group of users are being monitored;
   wherein the one or more preapproved care management devices are configured to redirect the notification signal to one or more caregivers on duty according to duty assignment of caregivers, date, and time of a work shift.

9. The incontinence underwear of claim 2, wherein the transceiver is configured to:
   perform two way communications with one or more preapproved cellular phones or one or more preapproved care management devices via a wireless communication protocol.

10. The incontinence underwear of claim 1, wherein the excretion collection unit further comprises:
    a feces collection unit, wherein the feces collection unit includes a feces collection bag, wherein the feces collection unit is washable and a used feces collection bag is replaced with a new feces collection bag.

11. A method of manufacturing an incontinence underwear, comprising:
    forming an interior layer includes an excretion area, wherein the excretion area includes one or more openings configured to drain excretions of a user away from the interior layer;
    forming a middle layer configured to house an excretion collection unit, wherein the excretion collection unit is configured to store the excretions from the interior layer, and wherein forming the middle layer further includes forming a feces sensing unit configured to detect feces discharged from the user, wherein comprises a moisture barrier having openings covered with a conductive gel;
    forming a feces monitoring module electrically coupled to the feces sensing unit, wherein the feces monitoring module is configured to monitor the feces sensing unit and communicate status of the feces sensing unit to one or more caregivers;
    forming an exterior layer configured to conceal and prevent leakage from the middle layer of the incontinence underwear; and
    forming a support frame configured to hold the interior layer, the middle layer and the exterior layer of the incontinence underwear together.

12. The method of claim 11, wherein forming the feces monitoring module comprises:

providing an RFID configured to associate the incontinence underwear and the user being monitored;

providing a processor configured to generate a notification signal to include the RFID and a feces sensed signal received from the feces sensing unit; and providing a transceiver configured to transmit the notification signal to one or more caregivers.

13. The method of claim 12, wherein forming the feces sensing unit comprises:

forming a galvanic sensor circuit configured to generate the feces sensed signal in response to feces being detected in the middle layer of the incontinence underwear.

14. The method of claim 13, wherein forming the galvanic sensor circuit comprises:

forming a cathode terminal;

forming an anode terminal;

wherein the cathode terminal and the anode terminal are ionically isolated by the moisture barrier in absence of discharged feces from the user; and wherein the cathode terminal and the anode terminal are ionically coupled together in response to the discharged feces from the user that form an ionic connection between the cathode terminal and the anode terminal, for the galvanic sensor circuit to generate the feces sensed signal.

15. The method of claim 14, wherein the cathode terminal comprises a cathodic sensing element, a cathodic salt bridge, and a cathode electrode, wherein the cathodic sensing element, the cathodic salt bridge, and the cathode electrode are ionically coupled together;

the anode terminal comprises an anodic sensing element, an anodic salt bridge, and an anode electrode, wherein the anodic sensing element, the anodic salt bridge, and the anode electrode are ionically coupled together; and wherein the ionic connection is formed between the cathodic sensing element and the anodic sensing element by the discharged feces from the user.

16. The method of claim 12, wherein providing the RFID comprises:

providing a passive RFID, wherein the passive RFID is powered by a current generated by the galvanic sensor circuit in response to the discharged feces from the user that forms an ionic connection between the cathode terminal and the anode terminal of the galvanic sensor circuit.

17. The method of claim 12, further comprises:

pairing the feces monitoring module with one or more preapproved cellular phones in situations where an individual user is being monitored;

directing the notification signal to a preapproved cellular phone of a caregiver; or directing the notification signal to a group of preapproved cellular phones of caregivers in a round-robin manner and in an order of a predetermined priority; or broadcasting the notification signal to the group of preapprove cellular phones of caregivers.

18. The method of claim 12, further comprises:

pairing the feces monitoring module with one or more preapproved care management devices in situations where a group of users are being monitored;

wherein the one or more preapproved care management devices are configured to redirect the notification signal to one or more caregivers on duty according to duty assignment of caregivers, date, and time of a work shift.

19. The method of claim 12, wherein providing the transceiver further comprises:

performing two way communications with one or more preapproved cellular phones or one or more preapproved care management devices via a wireless communication protocol.

20. The method of claim 11, wherein the excretion collection unit further comprises:

a feces collection unit, wherein the feces collection unit includes a feces collection bag, wherein the feces collection unit is washable and a used feces collection bag is replaced with a new feces collection bag.

* * * * *